US012618037B2

(12) United States Patent
Tanabe et al.

(10) Patent No.: US 12,618,037 B2
(45) Date of Patent: May 5, 2026

(54) CELL CULTURE VESSEL AND METHOD FOR CULTURING CELL

(71) Applicants: I Peace, Inc., Palo Alto, CA (US); FANUC CORPORATION, Yamanashi (JP)

(72) Inventors: Koji Tanabe, Palo Alto, CA (US); Ryoji Hiraide, Kyoto (JP); Kenta Suto, Palo Alto, CA (US); Kazunori Ban, Yamanashi (JP); Satoshi Kinoshita, Yamanashi (JP)

(73) Assignees: I Peace, Inc., Palo Alto, CA (US); FANUC CORPORATION, Yamanashi (JP)

( * ) Notice: Subject to any disclaimer, the term of this patent is extended or adjusted under 35 U.S.C. 154(b) by 930 days.

(21) Appl. No.: 17/645,675

(22) Filed: Dec. 22, 2021

(65) Prior Publication Data

US 2022/0195370 A1 Jun. 23, 2022

Related U.S. Application Data

(60) Provisional application No. 63/129,320, filed on Dec. 22, 2020.

(51) Int. Cl.
| | |
|---|---|
| *C12N 5/00* | (2006.01) |
| *C12M 1/00* | (2006.01) |
| *C12M 3/00* | (2006.01) |
| *C12N 5/074* | (2010.01) |
| *C12N 5/0775* | (2010.01) |
| *C12N 15/86* | (2006.01) |

(52) U.S. Cl.
CPC ............ *C12M 29/26* (2013.01); *C12M 23/44* (2013.01); *C12N 5/0662* (2013.01); *C12N 5/0696* (2013.01); *C12N 15/86* (2013.01); *C12N 2506/11* (2013.01); *C12N 2760/18841* (2013.01)

(58) Field of Classification Search
CPC ... C12M 23/44; C12N 5/0696; C12N 2506/45
See application file for complete search history.

(56) References Cited

U.S. PATENT DOCUMENTS

| | | | | |
|---|---|---|---|---|
| 5,017,490 A | * | 5/1991 | Taiariol | .................. C12M 23/14 |
| | | | | 435/294.1 |
| 11,525,111 B2 | * | 12/2022 | Gebauer | ................ C12M 27/16 |
| 2003/0017142 A1 | * | 1/2003 | Toner | .................. A61M 1/3472 |
| | | | | 435/370 |
| 2005/0239196 A1 | * | 10/2005 | Yanai | ..................... C12M 23/58 |
| | | | | 435/286.5 |
| 2007/0042490 A1 | * | 2/2007 | Welter | .................. C12M 21/08 |
| | | | | 435/325 |
| 2007/0224676 A1 | * | 9/2007 | Haq | ........................ C12M 41/44 |
| | | | | 435/298.2 |

(Continued)

FOREIGN PATENT DOCUMENTS

| | | | | |
|---|---|---|---|---|
| DE | 20209547 U1 | * | 9/2002 | ............ C12M 45/02 |
| JP | 2004-073084 A | | 3/2004 | |

(Continued)

*Primary Examiner* — Nathan A Bowers
(74) *Attorney, Agent, or Firm* — Studebaker Brackett PLLC

(57) ABSTRACT

A cell culture vessel comprising a housing in which a culture chamber is provided. In the housing, at least two holes that connect the outside of the housing and a culture chamber are provided.

3 Claims, 38 Drawing Sheets

(56) References Cited

U.S. PATENT DOCUMENTS

| 2009/0068742 | A1 |  | 3/2009 | Yamanaka |  |
|---|---|---|---|---|---|
| 2015/0252317 | A1 | * | 9/2015 | Lipkens | C12M 41/44 |
|  |  |  |  |  | 210/748.05 |
| 2015/0306641 | A1 |  | 10/2015 | Suzuki et al. |  |
| 2016/0201023 | A1 | * | 7/2016 | Tajima | C12M 21/08 |
|  |  |  |  |  | 435/325 |
| 2017/0342365 | A1 | * | 11/2017 | Nozaki | C12M 23/58 |
| 2018/0273892 | A1 | * | 9/2018 | Pizzi | C12M 45/02 |

FOREIGN PATENT DOCUMENTS

| JP | 4183742 | B1 | 11/2008 |
|---|---|---|---|
| JP | 2014-114997 | A | 6/2014 |

* cited by examiner

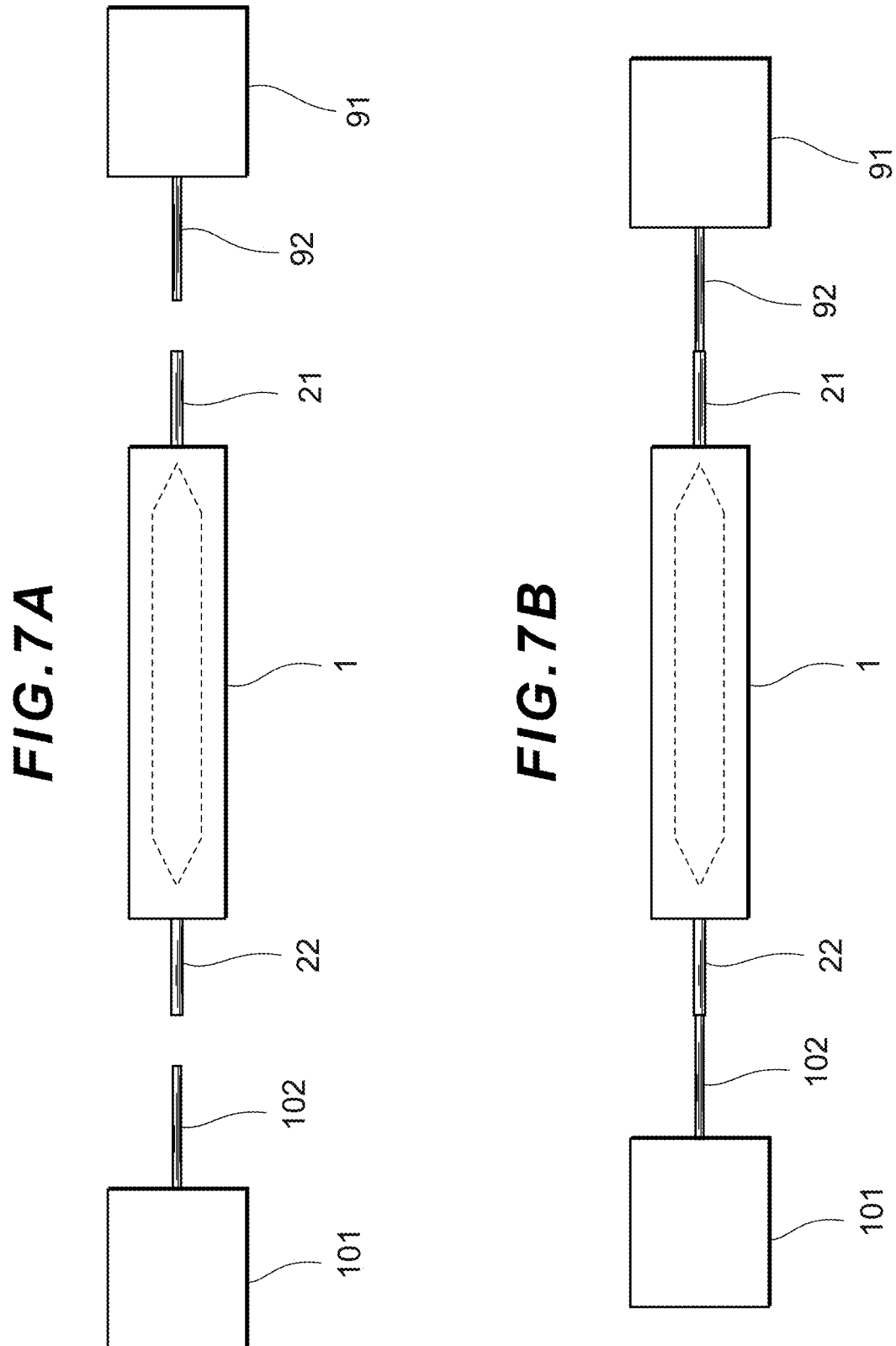

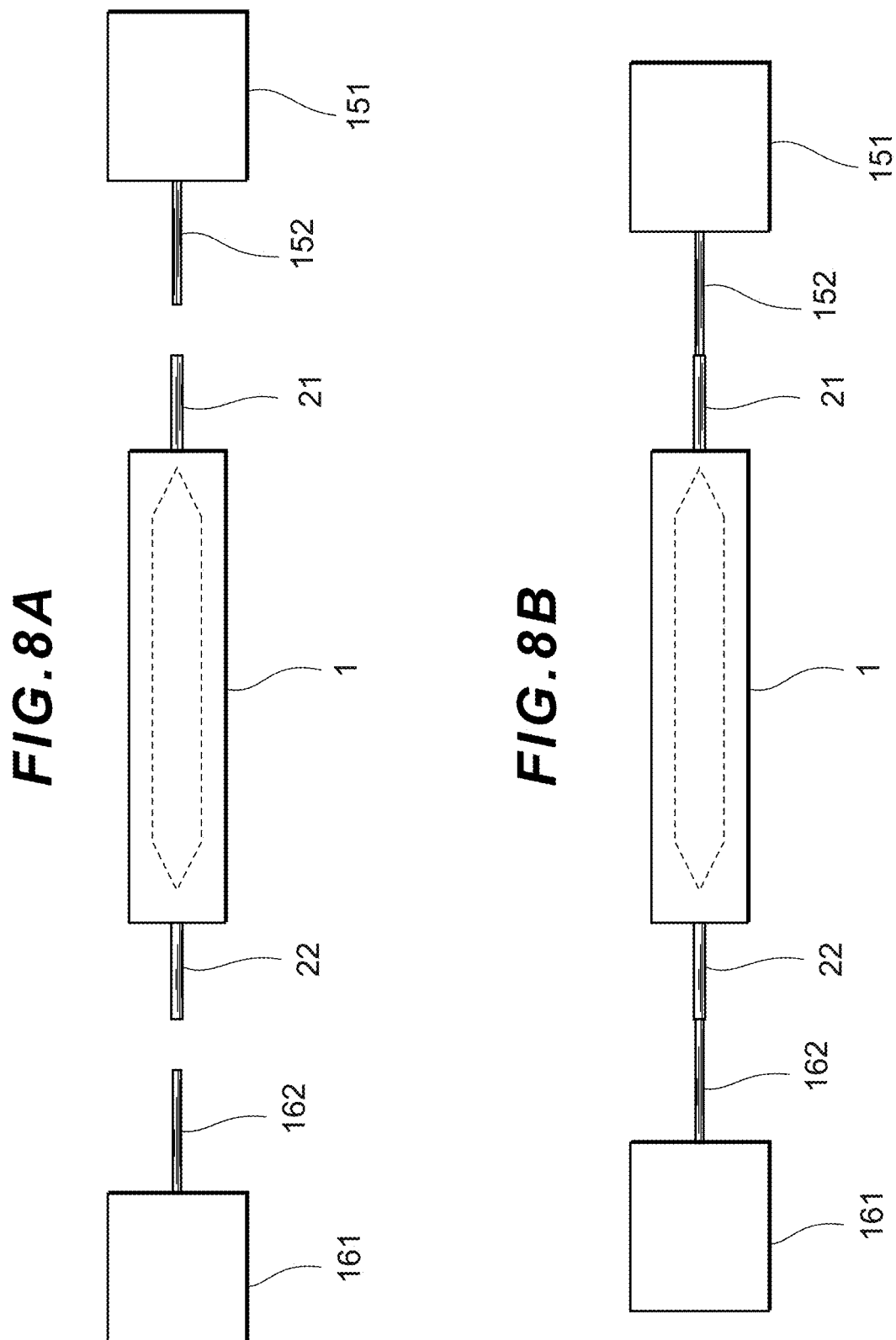

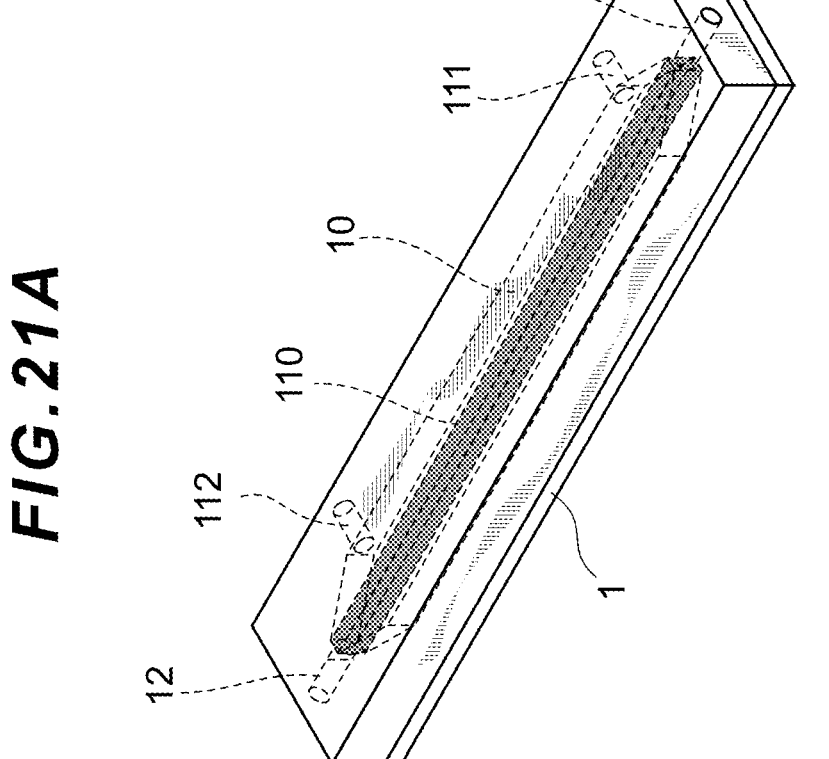

Day4

Day7

Day1

Day2

Day19

Day10

Day19

Day10

Passage2

Passage1

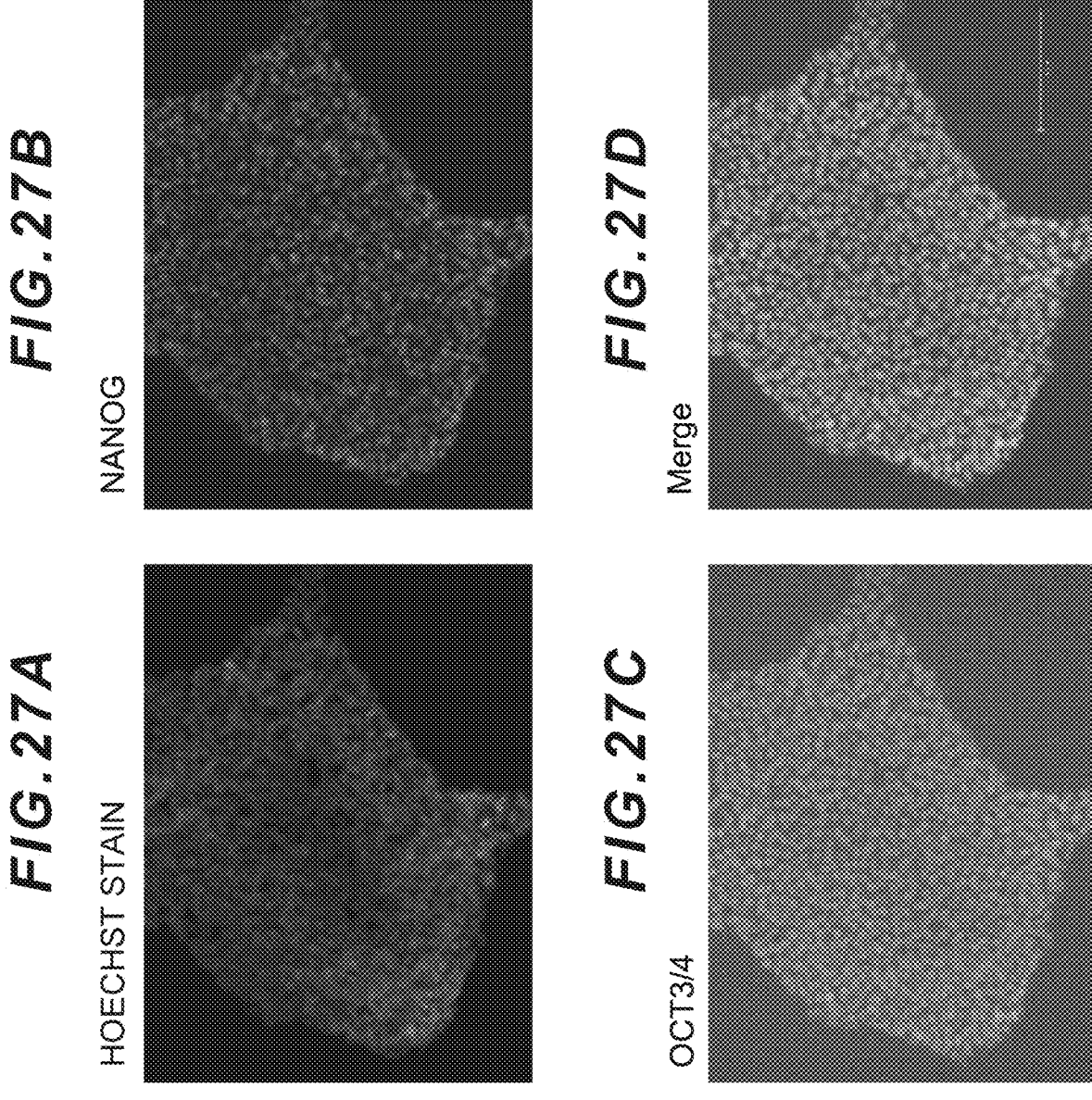
*FIG.27B*  NANOG
*FIG.27D*  Merge
*FIG.27A*  HOECHST STAIN
*FIG.27C*  OCT3/4

POSITIVE CONTROL

EXAMPLE

GFP (200619)

PHASE DIFFERENCE (200619)

FIG.30B

Day4

FIG.30D

Day10

FIG.30A

Day1

FIG.30C

Day7

OCT3/4

Merge

HOECHST STAIN

NANOG

LIN28

Merge

HOECHST STAIN

CELL CULTURE VESSEL AND METHOD FOR CULTURING CELL

BACKGROUND

Field

The present invention relates to a cell technology and relates to a cell culture vessel and a method for culturing a cell.

Description of Related Art

Embryonic stem cells (ES cells) are stem cells derived from early human or mouse embryos. ES cells have pluripotency that allows them to differentiate into any type of cells in a living body. Currently, human ES cells can be used for cell transplantation therapy for numerous diseases such as Parkinson's disease, juvenile diabetes, and leukemia. However, there are also obstacles to ES cell transplantation. In particular, ES cell transplantation can elicit immunorejection similar to a rejection response that follows unsuccessful organ transplantation. In addition, there are many criticisms and dissenting opinions from a moral point of view regarding use of ES cells derived by destroying human embryos.

Under such circumstances, Professor Shinya Yamanaka at Kyoto University succeeded in establishing induced pluripotent stem cells (iPS cells) by introducing four genes: OCT3/4, KLF4, c-MYC, and SOX2 into somatic cells. For this, Professor Yamanaka was awarded the 2012 Nobel Prize in Physiology or Medicine (for example, refer to Japanese Patent No. 4183742 and Patent Publication JP-A-2014-114997). iPS cells are ideal pluripotent cells without rejection responses or moral issues. Therefore, iPS cells are expected to be used for cell transplantation therapy.

SUMMARY

A technique that can efficiently culture not only iPS cells but also various cells is desired. Therefore, one objective of the present invention is to provide a cell culture vessel and a method for culturing a cell through which cells can be efficiently cultured.

According to an aspect of the present invention, there is provided a cell culture vessel comprising a housing in which a culture chamber is provided, wherein at least two holes that each connect the outside of the housing and the culture chamber are provided in the housing.

The cell culture vessel may further comprise connection flow paths that are connected to the holes.

In the cell culture vessel, the connection flow paths connected to the holes may be able to be blocked.

The cell culture vessel may further include variable volume containers connected to the two holes.

The cell culture vessel may further comprise connection flow paths connected to the variable volume containers.

In the cell culture vessel, the connection flow paths connected to the variable volume containers may be able to be blocked.

In the cell culture vessel, the inside of the housing and the inside of the variable volume container may form a closed space.

In the cell culture vessel, the inside of the housing and the inside of the variable volume container may not exchange a gas with the outside.

In the cell culture vessel, in the case where a fluid in any of the variable volume containers moves in a culture chamber of the housing, the volume of the variable volume container may change. The change may be contraction or expansion.

The cell culture vessel may comprising a plurality of housings.

In the cell culture vessel, the plurality of housings may be able to be separated from each other.

The cell culture vessel may further comprise a plurality of inter-housing flow paths that connect culture chambers of the plurality of housings.

According to an aspect of the present invention, there is provided a method for culturing a cell, including preparing a housing in which a culture chamber is provided, which is a housing in which at least two holes that connect the outside of the housing and the culture chamber are provided, contracting a variable volume container containing a cell therein, which is connected to any of the holes, expanding an expandable variable volume container which is connected to any of the holes, and moving the cell into the culture chamber of the housing, and culturing the cell in the culture chamber of the housing.

The method for culturing the cell may further include at least temporarily blocking a connection flow path that connects one of the holes and the variable volume container.

The method for culturing the cell may further include contracting a variable volume container containing a medium therein, which is connected to any of the holes, expanding an expandable variable volume container which is connected to any of the holes, and moving the medium into the culture chamber of the housing.

The method for culturing the cell may further include at least temporarily blocking a connection flow path that connects one of the holes and the contracted variable volume container.

The method for culturing the cell may further include at least temporarily blocking a connection flow path that connects one of the holes and the expanded variable volume container.

The method for culturing the cell may further include contracting a variable volume container containing a factor therein, which is connected to any of the holes, expanding an expandable variable volume container which is connected to any of the holes, moving the factor into the culture chamber of the housing, and introducing the factor into the cell.

The method for culturing the cell may further include at least temporarily blocking a connection flow path that connects one of the holes and the variable volume container containing the factor therein.

The method for culturing the cell may further include at least temporarily blocking a connection flow path that connects one of the holes and the variable volume container that is expanded by introducing the factor into the culture chamber.

The method for culturing the cell may further include contracting a variable volume container containing a dissociation reagent therein, which is connected to any of the holes, expanding an expandable variable volume container which is connected to any of the holes, moving the dissociation reagent into the culture chamber of the housing, and detaching the cell from the culture chamber.

The method for culturing the cell may further include at least temporarily blocking a connection flow path that connects one of the holes and the variable volume container containing the dissociation reagent therein.

The method for culturing the cell may further include at least temporarily blocking a connection flow path that connects one of the holes and the variable volume container that is expanded by introducing the dissociation reagent into the culture chamber.

According to an aspect of the present invention, there is provided a method for reprogramming a cell including culturing a cell in a housing in which a culture chamber is provided, which is a housing in which at least two holes that connect the outside of the housing and the culture chamber are provided, contracting a variable volume container containing a reprogramming factor therein, which is connected to any of the holes, expanding an expandable variable volume container which is connected to any of the holes, and moving the reprogramming factor into the culture chamber of the housing, and reprogramming the cell in the culture chamber of the housing.

The method for reprogramming the cell may further include at least temporarily blocking a connection flow path that connects one of the holes and the variable volume container.

The method for reprogramming the cell may further include at least temporarily blocking a connection flow path that connects one of the holes and the contracted variable volume container.

The method for reprogramming the cell may further include at least temporarily blocking a connection flow path that connects one of the holes and the expanded variable volume container.

According to an aspect of the present invention, there is provided a method for differentiating a cell, including culturing a cell in a housing in which a culture chamber is provided, which is a housing in which at least two holes that connect the outside of the housing and the culture chamber are provided, contracting a variable volume container containing a differentiating factor therein, which is connected to any of the holes, expanding an expandable variable volume container which is connected to any of the holes, and moving the differentiating factor into the culture chamber of the housing, and differentiating the cell in the culture chamber of the housing.

The method for differentiating the cell may further include at least temporarily blocking a connection flow path that connects one of the holes and the variable volume container.

The method for differentiating the cell may further include at least temporarily blocking a connection flow path that connects one of the holes and the contracted variable volume container.

The method for differentiating the cell may further include at least temporarily blocking a connection flow path that connects one of the holes and the expanded variable volume container.

According to the present invention, it is possible to provide a cell culture vessel and a method for culturing a cell through which cells can be efficiently cultured.

BRIEF DESCRIPTION OF DRAWINGS

FIG. 2A and FIG. 2B show schematic top views of the culture vessel according to the first embodiment;

FIG. 7A and FIG. 7B show schematic top views of the culture vessel according to the first embodiment;

FIG. 8A and FIG. 8B show schematic top views of the culture vessel according to the first embodiment;

FIG. 21A is a schematic perspective view of a culture vessel according to another embodiment, FIG. 21B is a schematic top view, and FIG. 21C is a schematic side view;

FIG. 22A is a schematic perspective view of a culture vessel according to another embodiment, FIG. 22B is a schematic top view, and FIG. 22C is a schematic side view;

FIG. 27A to FIG. 27D show microscope images of cells according to Example 3;

Figures 30A, 30B, 30C, 30D:
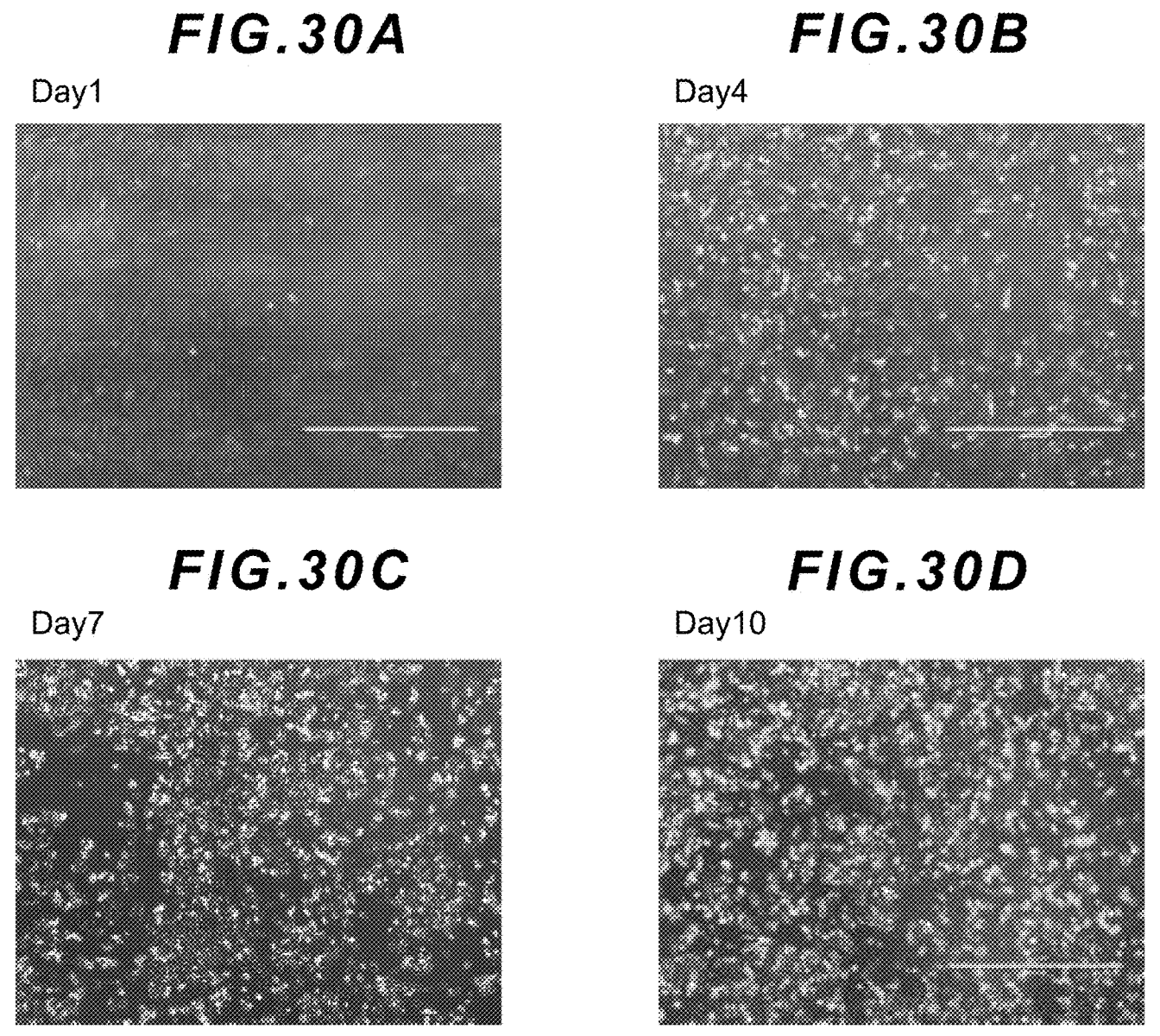

FIG. 30A to FIG. 30D show microscope images of cells according to Example 5;

DETAILED DESCRIPTION

Figure 1:
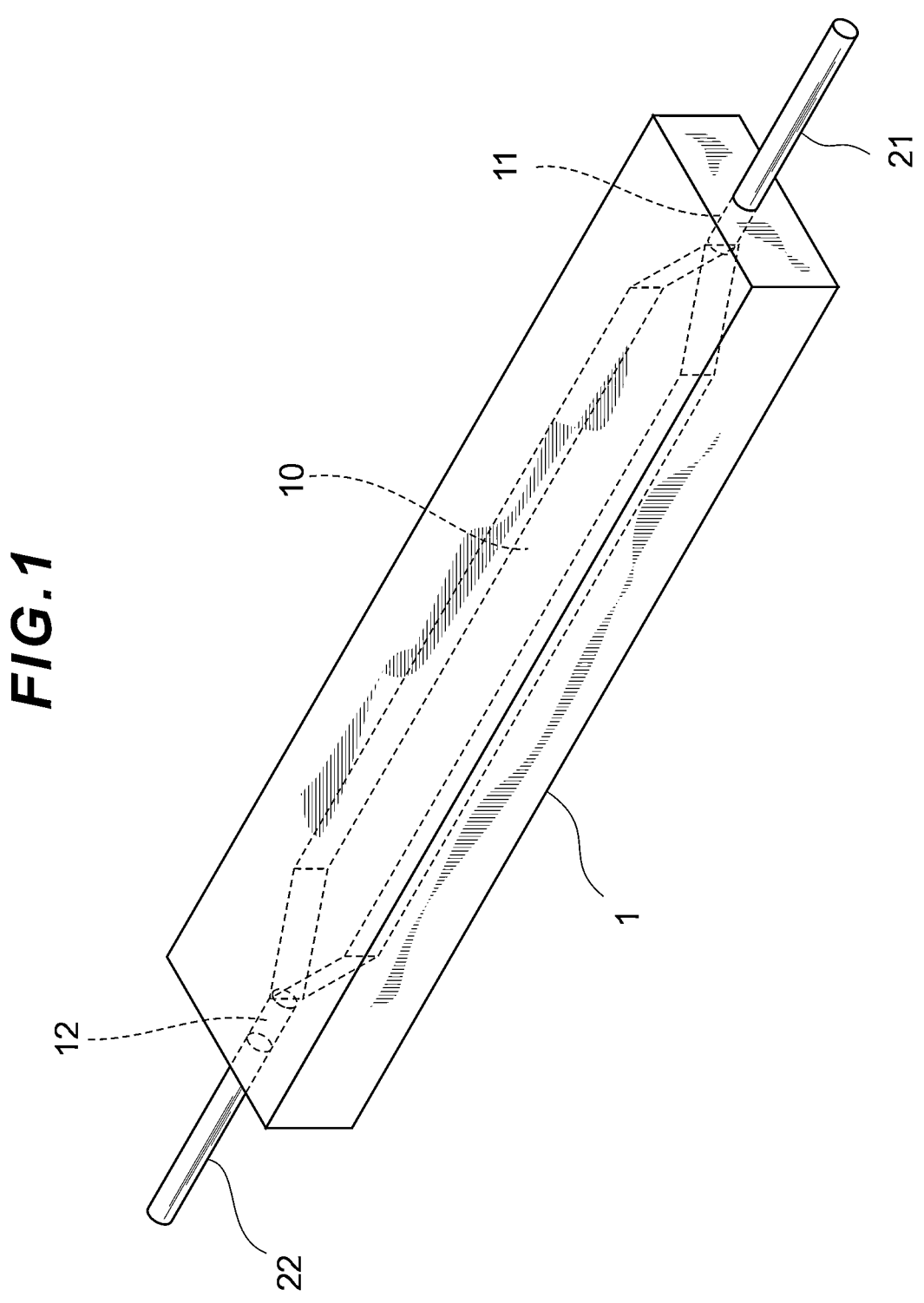
FIG. 1 is a schematic perspective view of a culture vessel according to a first embodiment.

Hereinafter, embodiments of the present invention will be described. In the following description of the drawings, the same or similar parts are denoted with the same or similar reference numerals. However, the drawings are schematic. Therefore, specific sizes and the like should be determined in light of the following description. In addition, it goes without saying that the drawings include parts having different size relationships and ratios with respect to each other.

First Embodiment

As shown in FIG. 1, a cell culture vessel according to a first embodiment includes a housing 1 in which a culture chamber 10 is provided. In the housing 1, a first hole 11 and a second hole 12 for connecting the outside of the housing 1 and the culture chamber 10 are provided. Cells are cultured in the culture chamber 10 of the housing 1. The culture chamber 10 is hollow. The size and shape of the culture chamber 10 are not particularly limited as long as cells can be cultured inside.

At least a part of the surface constituting the culture chamber 10 of the housing 1 may or may not be coated with a coating agent for cell adhesion. Examples of coating agents for cell adhesion include matrigel, collagen, polylysine, fibronectin, vitronectin, gelatin, and laminin. Alternatively, in the case where cells are suspended and cultured, at least a part of the surface constituting the culture chamber 10 of the housing 1 may be coated with a coating agent that inhibits cell adhesion. Examples of coating agents that restrict cell adhesion include poly(2-hydroxyethyl methacrylate). In addition, at least a part of the surface constituting the culture chamber 10 of the housing 1 may be hydrophilic. The inside of the housing 1 may be sterilized. Examples of sterilization treatments include a high-pressure steam sterilization treatment, radiation exposure with gamma rays and the like, and a sterilization treatment with UV radiation.

Examples of cells cultured in the culture vessel include somatic cells, but cells are not particularly limited. Examples of cells include fibroblasts, nerve cells, retinal epithelial cells, hepatocytes, β cells, renal cells, blood cells, dental pulp stem cells, keratinocytes, dermal papilla cells, oral epithelial cells, megakaryocytes, T cells, NK cells, NKT cells, chondrocytes, cardiomyocytes, muscle cells, vascular cells, epithelial cells, factor-introduced cells, reprogrammed cells, and stem cells, but cells are not particularly limited. Examples of stem cells include mesenchymal stem cells, somatic stem progenitor cells, pluripotent stem cells, ES cells, and iPS cells, but stem cells are not particularly limited.

The cells are contained in, for example, a medium. The medium is appropriately selected according to the type of cells. For example, in the case where the cells are somatic cells, a somatic cell medium such as a differentiated cell medium is selected. In the case where the cells are stem cells, a stem cell medium suitable for stem cells is selected. The medium may be a gel, a liquid, or a fluid solid. Examples of fluid solids include agar and a temperature-sensitive gel.

In the case where the medium is in gel state, the medium may contain a polymer compound. For example, the polymer compound may be at least one selected from the group consisting of gellan gum, deacylated gellan gum, hyaluronic acid, rhamsan gum, diutan gum, xanthan gum, carrageenan, fucoidan, pectin, pectic acid, pectinic acid, heparan sulfate, heparin, heparitin sulfate, keratosulfate, chondroitin sulfate, dermatan sulfate, rhamnan sulfate, and salts thereof. In addition, the medium may contain methyl cellulose.

Alternatively, the medium may contain a small amount of a temperature-sensitive gel selected from among poly(glycerol monomethacrylate) (PGMA), poly(2-hydroxypropyl methacrylate) (PHPMA), poly(N-isopropylacrylamide) (PNIPAM), amine terminated, carboxylic acid terminated, maleimide terminated, N-hydroxysuccinimide (NHS) ester terminated, triethoxysilane terminated, poly(N-isopropylacrylamide-co-acrylamide), poly(N-isopropylacrylamide-co-acrylic acid), poly(N-isopropylacrylamide-co-butylacrylate), poly(N-isopropylacrylamide-co-methacrylic acid), poly(N-isopropylacrylamide-co-methacrylic acid-co-octadecyl acrylate), and N-Isopropylacrylamide. Here, in the present disclosure, the gel-like medium or gel medium includes a polymer medium.

For example, the housing 1 is configured to make the inside closed off from the outside air. The material of the housing 1 is selected such that, for example, the inside does not exchange gases, viruses, microorganisms, impurities, and the like with the outside through the wall of the housing 1. Examples of materials of the housing 1 include a resin and glass. The housing 1 may be transparent.

For example, a first connection flow path 21 is connected to the first hole 11 of the housing 1. In addition, for example, a second connection flow path 22 is connected to the second hole 12 of the housing 1. Each of the first connection flow path 21 and the second connection flow path 22 is, for example, a flexible tube. Each of the first connection flow path 21 and the second connection flow path 22 is made of, for example, a resin. The resin is, for example, a synthetic resin. Examples of synthetic resins include polyvinyl chloride. For example, each of the first connection flow path 21 and the second connection flow path 22 can be blocked.

For example, in the case where each of the first connection flow path 21 and the second connection flow path 22 is made of a resin, each of the first connection flow path 21 and the second connection flow path 22 is interposed by a pressurizer while they are heated, and thus each of the first connection flow path 21 and the second connection flow path 22 is blocked. For example, the housing 1 is produced in a clean environment, the housing 1 is connected to the first connection flow path 21 and the second connection flow path 22 in a clean environment, the first connection flow path 21 and the second connection flow path 22 are blocked, and thus it is possible to maintain the inside of the first connection flow path 21 and the second connection flow path 22 and the inside of the housing 1 in a clean environment. It should be noted that a method for blocking a flow path is not limited to the above, and optical processing, laser light processing, friction processing, rubbing processing, thermal processing without pressurization, pressurization processing without heating or the like can be used. For example, the flow paths may be interposed by a clip.

Figures 2A, 2B:
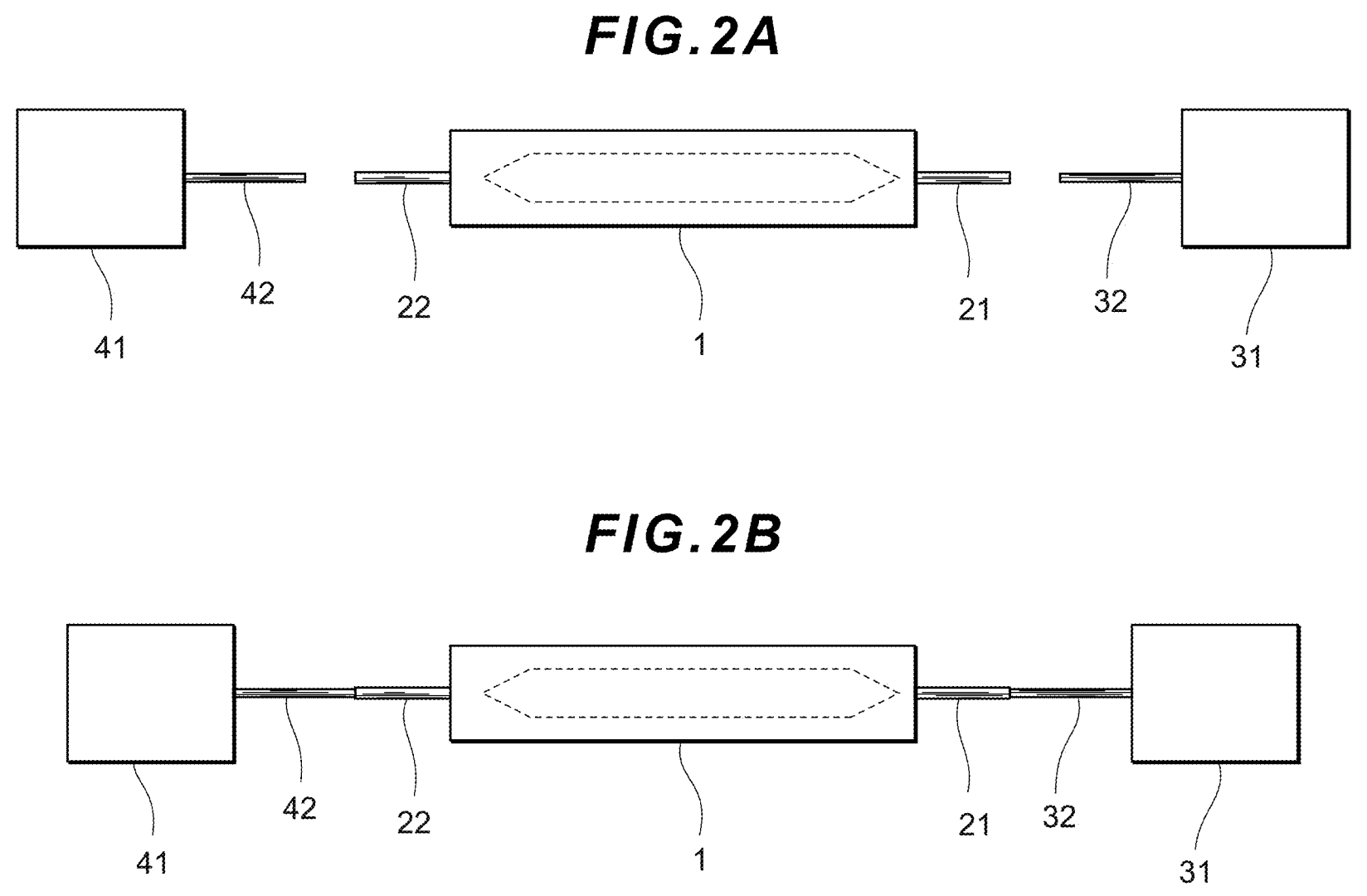

As shown in FIG. 2A and FIG. 2B, a variable volume container 31 containing a solution containing cells is connected to the first hole 11 of the housing 1, for example, via the first connection flow path 21. The solution is, for example, a medium. An expandable variable volume container 41 which is empty or contains any fluid is connected to the second hole 12 of the housing 1, for example, via the second connection flow path 22. The variable volume container 31 containing the solution containing the cells may be placed in a temperature control chamber that can be set to a temperature suitable for the cells until it is connected to the housing 1.

Each of the variable volume container 31 and the variable volume container 41 includes, for example, a syringe containing a fluid and a plunger which is inserted into the syringe and movable in the syringe, and the volume available for containing the fluid in the syringe can be changed by moving the plunger. Alternatively, each of the variable volume container 31 and the variable volume container 41 may be a flexible bellows or bag. The variable volume container 31 and the variable volume container 41 may be the same container except for contents.

A first connection flow path 32 is connected to the variable volume container 31. A second connection flow path 42 is connected to the variable volume container 41. Each of the first connection flow path 32 and the second connection flow path 42 is, for example, a flexible tube. Each of the first connection flow path 32 and the second connection flow path 42 is made of, for example, a resin. The resin is, for example, a synthetic resin. Examples of synthetic resins include polyvinyl chloride. For example, each of the first connection flow path 32 and the second connection flow path 42 can be blocked.

For example, the first connection flow path 32 whose end is blocked and the first connection flow path 21 whose end is blocked are bonded by an sterile welder, and a path from the first connection flow path 32 to the first connection flow path 21 may be opened. In addition, for example, the second connection flow path 22 whose end is blocked and the second connection flow path 42 whose end is blocked are bonded by an sterile welder, and a path from the second connection flow path 22 to the second connection flow path 42 may be opened.

Figure 3A:
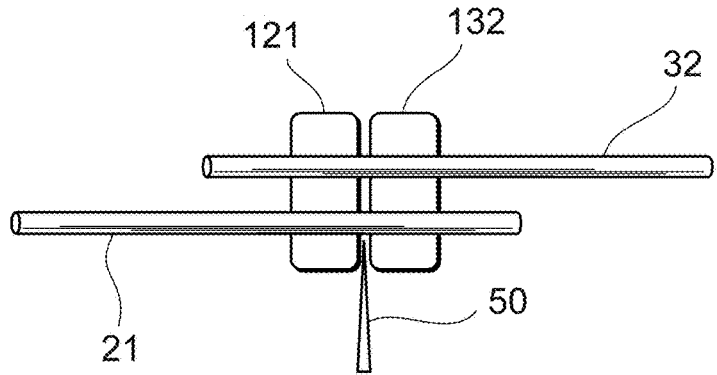
FIG. 3A to FIG. 3C show schematic views of a sterile welder according to the first embodiment.
Figure 3B:
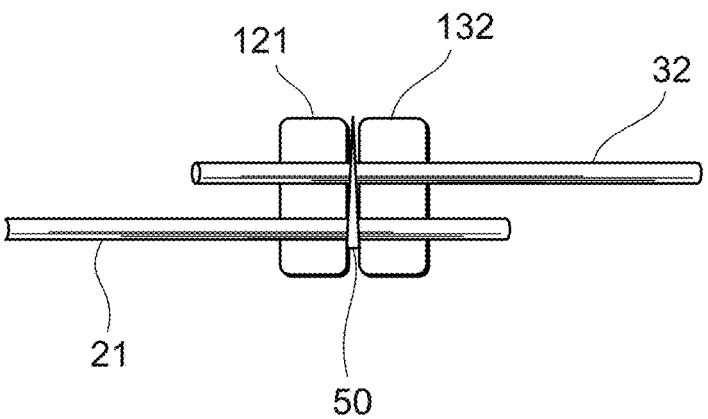

As shown in FIG. 3A, the sterile welder includes holders 121, 132 that hold the first connection flow path 32 and the first connection flow path 21 that are partially arranged in parallel, and a cutter 50 that can move between the holders 121, 132. The cutter 50 can be heated. As shown in FIG. 3B, the cutter 50 moves between the holders 121, 132, and melts and cuts each of the first connection flow path 32 and the first connection flow path 21. Each melt-cut part of the first connection flow path 32 and the first connection flow path 21 is in close contact with the side surface of the cutter 50, and the outside air does not enter the inside of the first connection flow path 32 and the first connection flow path 21.

Figure 3C:
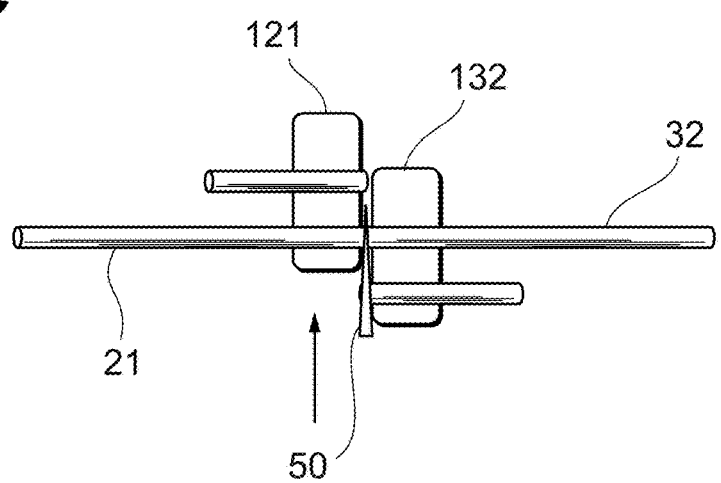

As shown in FIG. 3C, while each melt-cut part of the first connection flow path 32 and the first connection flow path 21 is in close contact with the side surface of the cutter 50, at least one of the holders 121, 132 is moved, and the melt-cut parts of the first connection flow path 32 and the first connection flow path 21 are arranged on the same line.

Figure 4A:
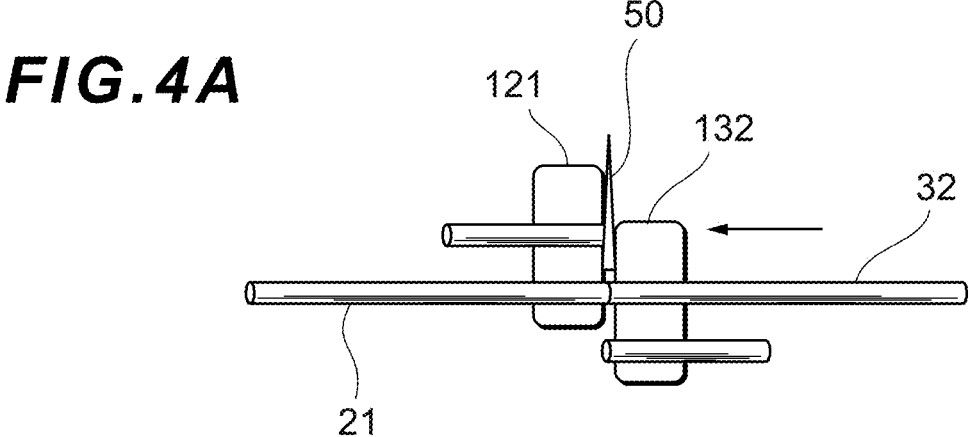
FIG. 4A and FIG. 4B show schematic views of the sterile welder according to the first embodiment.
Figure 4B:
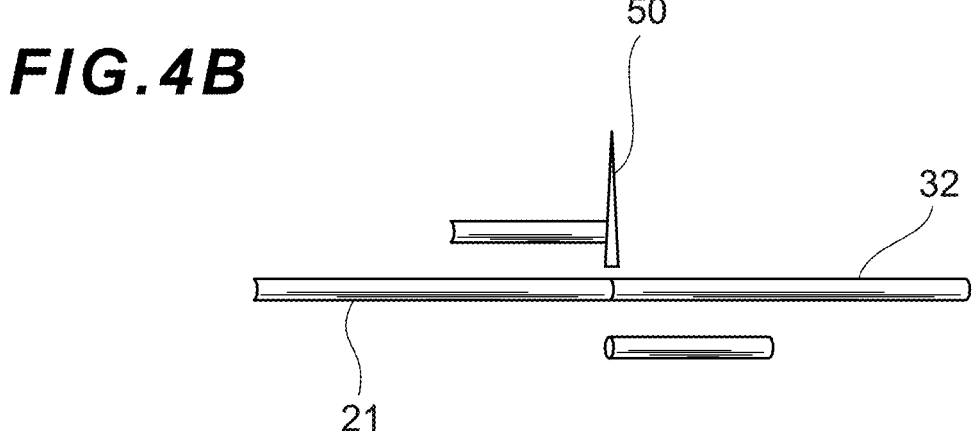

As shown in FIG. 4A and FIG. 4B, the cutter 50 between the melt-cut parts of the first connection flow path 32 and the first connection flow path 21 is removed, and at the same time, the melt-cut parts of the first connection flow path 32 and the first connection flow path 21 are bonded to each other. Thereby, it is possible to sterilely bond the first connection flow path 32 and the first connection flow path 21 without allowing the outside air to enter the inside of the first connection flow path 32 and the first connection flow path 21. Then, the first connection flow path 32 and the first connection flow path 21 are removed from the holders 121, 132. According to the same procedure, the second connection flow path 22 and the second connection flow path 42 can be sterilely bonded by the sterile welder.

In the case where the variable volume container 31 and the variable volume container 41 are connected to the housing 1, the inside of the housing 1 and the inside of the variable volume container 31 and the variable volume container 41 form a closed space.

As shown in FIG. 2A and FIG. 2B, in the case where the volume of the variable volume container 31 containing the solution containing the cells therein changes and contracts, and the volume of the variable volume container 41 which is empty or contains any fluid changes and expands, a gas such as air in the culture chamber 10 of the housing 1 moves into the variable volume container 41 via the second hole 12, the second connection flow path 22, and the second connection flow path 42. In addition, the solution containing the cells in the variable volume container 31 moves into the culture chamber 10 of the housing 1 via the first connection flow path 32, the first connection flow path 21, and the first hole 11. The inside of the culture chamber 10 may be filled with the solution containing the cells so that no air layer remains in the culture chamber 10. However, micro bubbles may remain in the solution filled into the culture chamber 10 as long as no air layer remains. In the case where the solution containing the cells is filled in so that no air layer remains in the culture chamber 10, the pH of the solution containing the cells is stable.

Alternatively, the solution containing the cells may be put into the culture chamber 10 so that an air layer of carbon dioxide is formed in the culture chamber 10. In this case, for example, carbon dioxide may be put into the variable volume container 31 containing the solution containing the cells.

The volume of the variable volume container 31 may be actively contracted or passively contracted. The volume of the variable volume container 41 may be actively expanded or passively expanded. For example, an operator may contract the volume of the variable volume container 31. In this case, the inside of the variable volume container 41 receives the pressure of the fluid discharged from the variable volume container 31 and the volume of the variable volume container 41 expands.

After the solution containing the cells is moved into the culture chamber 10 of the housing 1, the cells may be cultured while the variable volume container 31 is connected to the first connection flow path 21 and the variable volume container 41 is connected to the second connection flow path 22. Thereby, it is possible to culture the cells in a closed space. Alternatively, for example, by blocking the first connection flow path 21 or the first connection flow path 32 and the second connection flow path 22 or the second connection flow path 42, it is possible to culture cells in a closed space. Regarding a method for blocking the first connection flow path 21 or the first connection flow path 32 and the second connection flow path 22 or the second connection flow path 42, thermocompression bonding may be exemplified. After the first connection flow path 21 or the first connection flow path 32 is blocked, the variable volume container 31 that contained the cells may be removed from the first connection flow path 21 or the first connection flow path 32. After the second connection flow path 22 or the second connection flow path 42 is blocked, the variable volume container 41 may be removed from the second connection flow path 22 or the second connection flow path 42. After the variable volume container 31 and the variable volume container 41 are removed, the housing 1 may be placed in a temperature control chamber that can be set to a temperature suitable for cell culture.

Figures 5A, 5B:
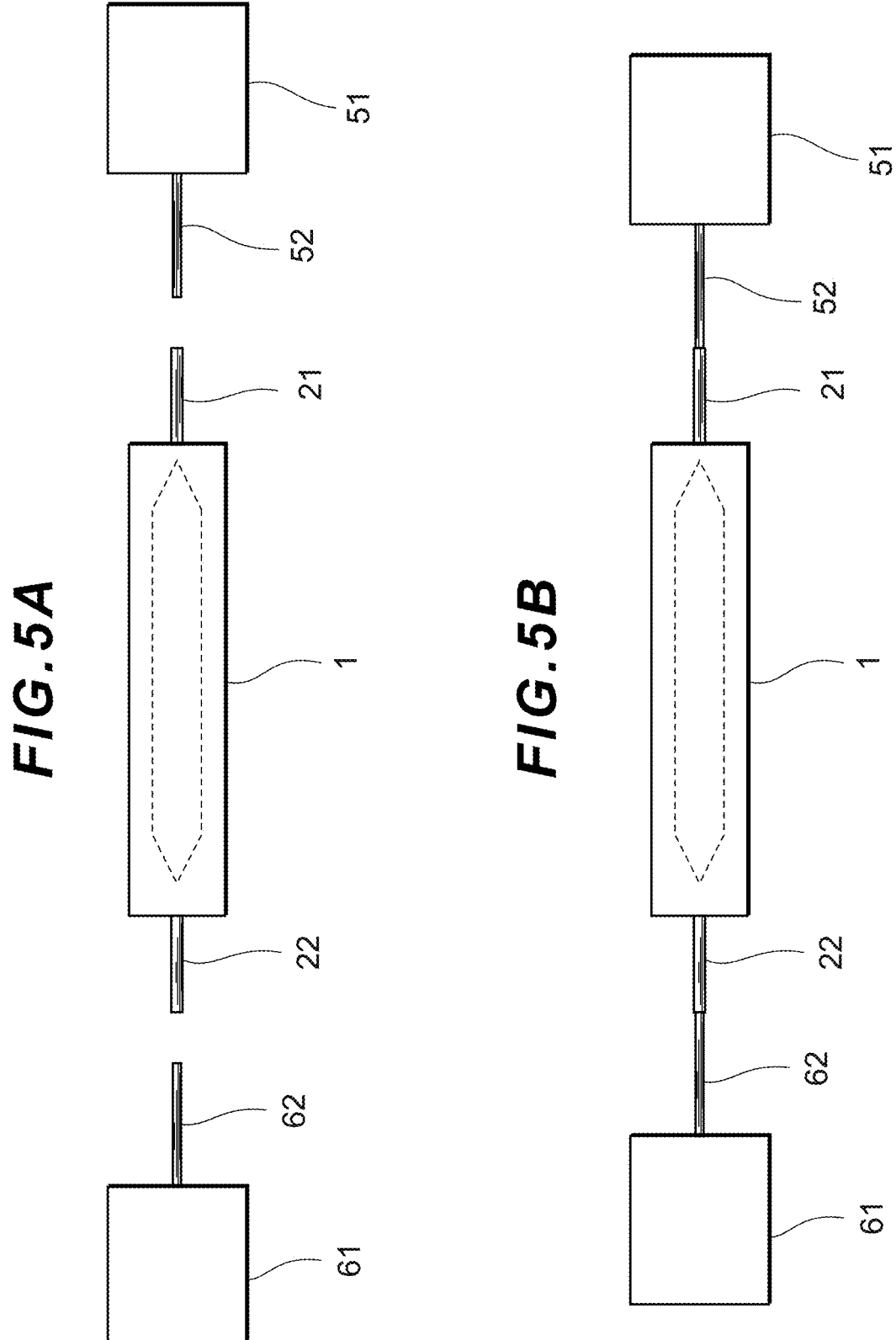
FIG. 5A and FIG. 5B show schematic top views of the culture vessel according to the first embodiment.

In the case where the medium in the culture chamber 10 of the housing 1 is replaced while culturing the cells in the culture chamber 10 of the housing 1, as shown in FIG. 5A and FIG. 5B, a variable volume container 51 containing a solution containing a medium is connected to the first connection flow path 21, and an expandable variable volume container 61 which is empty or contains any fluid is connected to the second connection flow path 22. The variable volume container 51 containing the medium may be placed in a temperature control chamber that can be set to a temperature suitable for the medium before it is connected to the housing 1.

In the case where the volume of the variable volume container 51 containing the medium therein changes and contracts, and the volume of the variable volume container 61 which is empty or contains any fluid changes and expands, the medium in the culture chamber 10 of the housing 1 moves into the variable volume container 61 via the second hole 12, the second connection flow path 22, and a second connection flow path 62. In addition, the medium in the variable volume container 51 moves into the culture chamber 10 of the housing 1 via a first connection flow path 52, the first connection flow path 21, and the first hole 11. Thereby, the medium in the culture chamber 10 of the housing 1 is replaced. The inside of the culture chamber 10 may be filled with the medium so that no air layer remains in the culture chamber 10. However, as long as no air layer remains, micro bubbles may remain in the medium filled into the culture chamber 10. In the case where the medium is filled in so that no air layer remains in the culture chamber 10, the pH of the medium is stable. Alternatively, the medium may be put into the culture chamber 10 so that an air layer of carbon dioxide is formed in the culture chamber 10. In this case, for example, carbon dioxide may be put into the variable volume container 51 containing a medium.

Replacement of the medium may be performed a plurality of times. For example, the variable volume container 51 containing the medium connected to the first connection flow path 21 may be replaced a plurality of times, and the medium may be introduced into the culture chamber 10 of the housing 1 a plurality of times. In addition, the medium may be replaced by changing the type of the medium according to the state of the cells. Alternatively, the medium may be moved into the culture chamber 10 of the housing 1 from the variable volume container 51 containing the medium a plurality of times in a divided manner.

After the medium is replaced, the cells may be cultured while the variable volume container 51 is connected to the first connection flow path 21 and the variable volume container 61 is connected to the second connection flow path 22. Thereby, it is possible to culture the cells in a closed space. Alternatively, for example, by blocking the first connection flow path 21 or the first connection flow path 52 and the second connection flow path 22 or the second connection flow path 62, it is possible to culture the cells in a closed space again. After the first connection flow path 21 or the first connection flow path 52 is blocked, the variable volume container 51 that contained the medium may be removed from the first connection flow path 21 or the first connection flow path 52. After the second connection flow path 22 or the second connection flow path 62 is blocked, the variable volume container 61 may be removed from the second connection flow path 22 or the second connection flow path 62. After the variable volume container 51 and the variable volume container 61 are removed, the housing 1 may be placed in a temperature control chamber that can be set to a temperature suitable for cell culture.

Figures 6A, 6B:
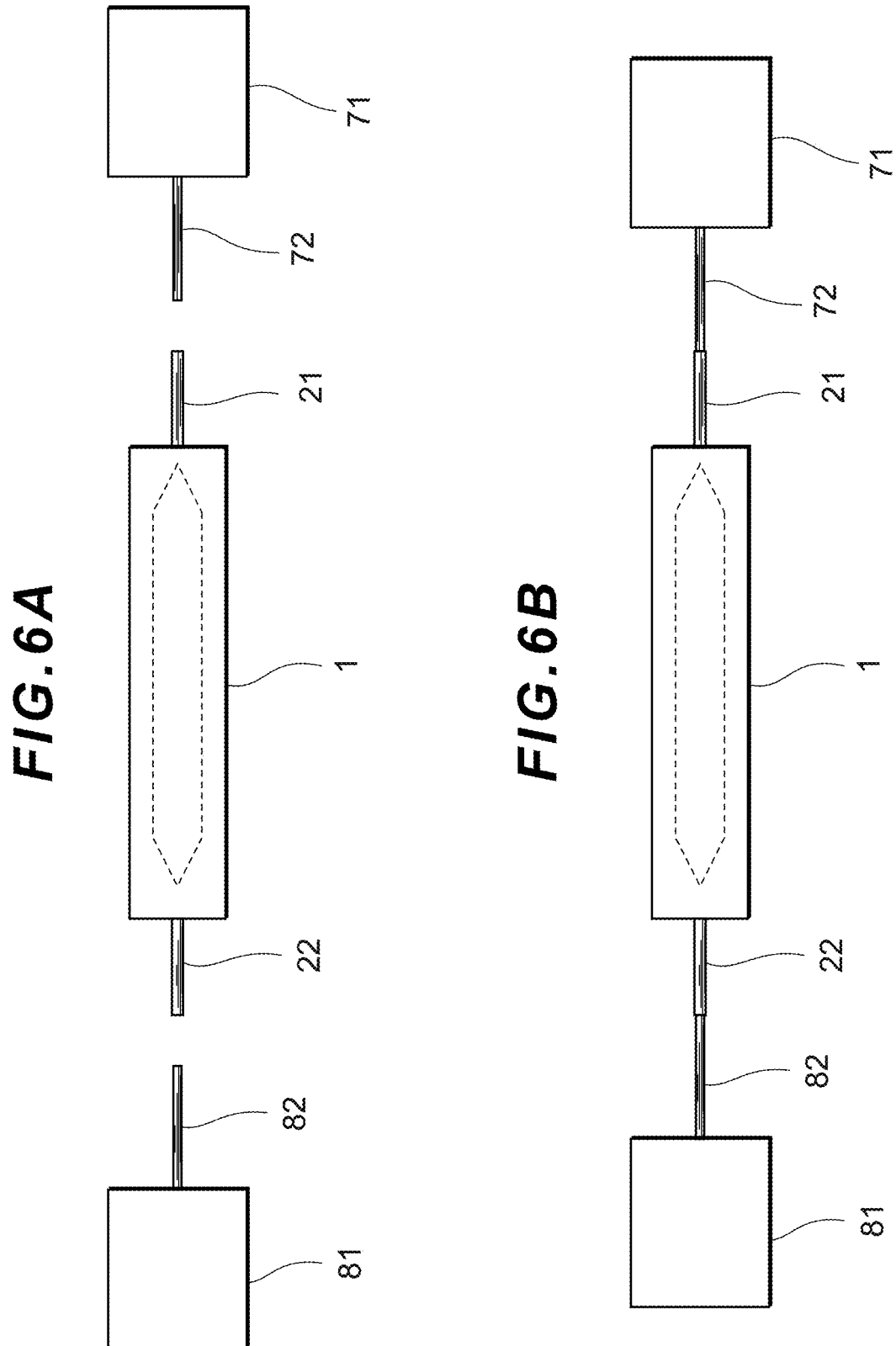
FIG. 6A and FIG. 6B show schematic top views of the culture vessel according to the first embodiment.

In the case where a factor is introduced into the cells cultured in the culture chamber 10 of the housing 1, as shown in FIG. 6A and FIG. 6B, a variable volume container 71 containing a solution containing a factor therein is connected to the first connection flow path 21, and an expandable variable volume container 81 which is empty or contains any fluid is connected to the second connection flow path 22. The variable volume container 71 containing the solution containing the factor may be placed in a temperature control chamber that can be set to a temperature suitable for the factor before it is connected to the housing 1.

The factor may be a nucleic acid such as DNA, RNA, and an oligonucleotide, and may be a protein, a compound, or a virus. The DNA may be plasmid DNA. The RNA may be mRNA, siRNA, or miRNA. The RNA may be modified RNA or unmodified RNA. The nucleic acid may be incorporated into a vector. Examples of vectors include plasmids, retroviruses, lentiviruses, adenoviruses, adeno-associated viruses, episomal, and Sendai viruses. The protein may be a nuclease protein such as Cas9 protein. The virus may be a lentivirus. The factor may be an inducing factor that induces cells in a first state into cells in a second state. The factor may be a hormone, a growth factor, or a low-molecular-weight compound.

In the present disclosure, induction refers to reprogramming, initialization, transformation, transdifferentiation (Transdifferentiation or Lineage reprogramming), differentiation induction, cell fate change (Cell fate reprogramming) or the like. A factor that induces cells other than pluripotent stem cells into pluripotent stem cells is called a reprogramming factor. Examples of reprogramming factors include OCT3/4, SOX2, KLF4, and c-MYC. In addition, reprogramming factors also include, for example, growth factors such as bFGF and TGF-β and compounds. In addition, a factor that induces certain cells into differentiated cells is called a differentiating factor. The differentiating factor induces stem cells into differentiated cells. Alternatively, the differentiating factor induces somatic cells other than stem cells into other somatic cells. The differentiating factor includes growth factors such as activin, bone morphogenetic proteins, and FGF, and compounds such as GSK inhibitors and smad inhibitors. Induction of somatic cells other than stem cells into somatic cells other than stem cells may be referred to as direct reprogramming.

Examples of factors that induce cells into nervous system cells include ASCL family, DLX family, MYT family, NeuroD family, SOX family, and NGN family. Examples of ASCL family include ASCL1. Examples of DLX family include DLX2. Examples of MYT family include MYT1L. Examples of NGN family include NGN2. Examples of nervous system cells include nerve cells, neural stem cells and neural progenitor cells. Examples of nerve cells include inhibitory nerve cells, excitatory nerve cells, dopamin-producing nerve cells, cranial nerves, intervening nerves, and optic nerves. Alternatively, nervous system cells may be motor nerve cells, oligodendrocyte progenitor cells, astrocytes, oligodendrocytes or the like.

Examples of factors that induce cells into cardiomyocytes include GATA family, MEF family, TBX family, MYOCD family, MESP family, and miR-133 family. Examples of GATA family include GATA4A. Examples of MEF family include MEF2C. Examples of TBX family include TBX5. Examples of MESP family include MESP1.

In the case where the volume of the variable volume container 71 containing the solution containing the factor therein changes and contracts, and the volume of the variable volume container 81 which is empty or contains any fluid changes and expands, the solution in the culture chamber 10 of the housing 1 moves into the variable volume container 81 via the second hole 12, the second connection flow path 22, and a second connection flow path 82. In addition, the solution containing the factor in the variable volume container 71 moves into the culture chamber 10 of the housing 1 via a first connection flow path 72, the first connection flow path 21, and the first hole 11. Thereby, the factor comes into contact with cells in the culture chamber 10 of the housing 1 and the factor is introduced into the cells.

After the solution containing the factor is moved into the culture chamber 10 of the housing 1, the factor may be introduced into cells while the variable volume container 71 is connected to the first connection flow path 21 and the variable volume container 81 is connected to the second connection flow path 22. Thereby, it is possible to introduce the factor into the cells in a closed space. Alternatively, for example, by blocking the first connection flow path 21 or the first connection flow path 72 and the second connection flow path 22 or the second connection flow path 82, it is possible to introduce the factor into the cells in a closed space. After the first connection flow path 21 or the first connection flow path 72 is blocked, the variable volume container 71 containing the factor may be removed from the first connection flow path 21 or the first connection flow path 72. After the second connection flow path 22 or the second connection flow path 82 is blocked, the variable volume container 81 may be removed from the second connection flow path 22 or the second connection flow path 82. After the variable volume container 71 and the variable volume container 81 are removed, the housing 1 may be placed in a temperature control chamber that can be set to a temperature suitable for introducing the factor.

Introduction of the factor into the cells may be performed a plurality of times. For example, the variable volume container 71 containing the solution containing the factor connected to the first connection flow path 21 may be replaced a plurality of times, and introduction of the factor into the cells may be performed a plurality of times. Alternatively, the solution containing the factor may be moved into the culture chamber 10 of the housing 1 from the variable volume container 71 containing the solution containing the factor a plurality of times in a divided manner. In addition, after the factor is introduced into the cells, according to the same procedure as medium replacement, the solution containing the factor in the culture chamber 10 of the housing 1 is replaced with a medium, and cell culture may be continued. In addition, according to the above procedure, the medium may be repeatedly replaced. The culture includes initialization culture and expansion culture.

In the case where the cells cultured in the culture chamber 10 of the housing 1 are detached from the culture chamber 10, as shown in FIG. 7A and FIG. 7B, a variable volume container 91 containing a solution containing a dissociation reagent therein is connected to the first connection flow path 21, and an expandable variable volume container 101 which is empty or contains any fluid is connected to the second connection flow path 22. Examples of dissociation reagents include trypsin, triple select, accutase, and EDTA. The variable volume container 91 containing the solution containing the dissociation reagent may be placed in a temperature control chamber that can be set to a temperature suitable for the dissociation reagent before it is connected to the housing 1.

In the case where the volume of the variable volume container 91 containing the solution containing the dissociation reagent therein changes and contracts, and the volume of the variable volume container 101 which is empty or contains any fluid changes and expands, the solution in the culture chamber 10 of the housing 1 moves into the variable volume container 101 via the second hole 12, the second connection flow path 22, and a second connection flow path 102. In addition, the solution containing the dissociation reagent in the variable volume container 91 moves into the culture chamber 10 of the housing 1 via a first connection flow path 92, the first connection flow path 21, and the first hole 11. Thereby, the solution containing the dissociation reagent comes into contact with the cells in the culture chamber 10 of the housing 1.

After the dissociation reagent is moved into the culture chamber 10 of the housing 1, the dissociation reagent may be brought into contact with the cells while the variable volume container 91 is connected to the first connection flow path 21 and the variable volume container 101 is connected to the second connection flow path 22. In addition, the volume of the variable volume container 91 containing air therein further contracts, the volume of the variable volume container 101 expands, and thus the dissociation reagent in the culture chamber 10 may be moved into the variable volume container 101. After the first connection flow path 21 or the first connection flow path 92 is blocked, the variable volume container 91 that contained the dissociation reagent may be removed from the first connection flow path 21 or the first connection flow path 92. After the second connection flow path 22 or the second connection flow path 102 is blocked, the variable volume container 101 may be removed from the second connection flow path 22 or the second connection flow path 102. After the variable volume container 91 and the variable volume container 101 are removed, the housing 1 may be placed in a temperature control chamber that can be set to a temperature suitable for detaching the cells. The detached cells may be seeded in the same or different housing 1, and the cells may be passaged. During passage, the collected cells may be seeded without distinction in the housing without colony picking.

As shown in FIG. 8A and FIG. 8B, in the case where the cells in the culture chamber 10 of the housing 1 are collected, a variable volume container 151 containing a cryopreservation solution therein is connected to the first connection flow path 21, and an expandable variable volume container 161 which is empty or contains any fluid is connected to the second connection flow path 22. The variable volume container 151 containing the cryopreservation solution may be placed in a temperature control chamber that can be set to a temperature suitable for the cryopreservation solution before it is connected to the housing 1.

In the case where the volume of the variable volume container 151 containing the cryopreservation solution therein changes and contracts, and the volume of the variable volume container 161 which is empty or contains any fluid changes and expands, a gas and/or a solution in the culture chamber 10 of the housing 1 moves into the variable volume container 161 via the second hole 12, the second connection flow path 22, and a second connection flow path 162. In addition, the cryopreservation solution in the variable volume container 151 moves in the culture chamber 10 of the housing 1 via a first connection flow path 152, the first connection flow path 21, and the first hole 11. Thereby, the cryopreservation solution comes into contact with cells in the culture chamber 10 of the housing 1. Then, the housing 1 may be shaken to promote detachment of the cells from the culture chamber 10.

After the cells are detached from the culture chamber 10, in the case where the volume of the variable volume container 151 further contracts, and the volume of the variable volume container 161 expands, the cells in the culture chamber 10 move into the variable volume container 161. Thereby, the cells can be collected.

After the cells are stored in the variable volume container 161, the second connection flow path 162 is blocked, the housing 1 can be removed from the variable volume container 161 by cutting any part of the second connection flow paths 22 and 162 between a blocked part of the second connection flow path 162 and the housing 1. Alternatively, after the cells are stored in the variable volume container 161, the second connection flow path 22 is blocked, the housing 1 can be removed from the variable volume container 161 by cutting any part of the second connection flow path 22 between a blocked part of the second connection flow path 22 and the housing 1.

Figure 9:
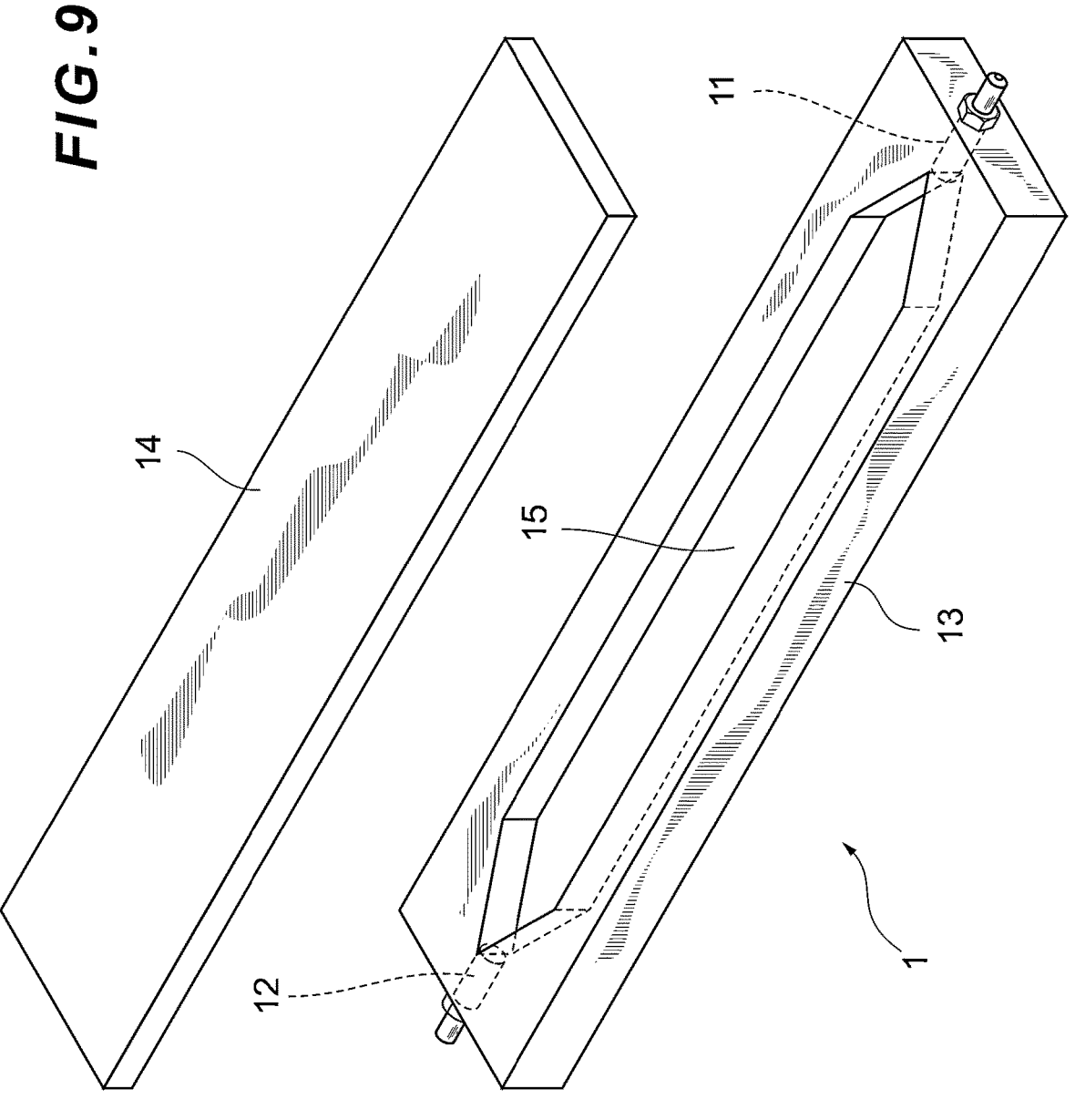
FIG. 9 is a schematic exploded perspective view of the culture vessel according to the first embodiment.

Next, a method for manufacturing the housing 1 according to the first embodiment will be described. As shown in FIG. 9, a housing base 13 in which a concave part 15 and the first hole 11 and the second hole 12 connected to the concave part 15 are provided is prepared. In addition, a cover 14 that can cover the concave part 15 of the housing base 13 is prepared. The surface forming the concave part 15 of the housing base 13 may be coated with a coating agent for cell adhesion. Alternatively, the surface of the cover 14 that covers the concave part 15 of the housing base 13 may be coated with a coating agent for cell adhesion. In the case where the concave part 15 of the housing base 13 is covered with the cover 14, the housing 1 shown in FIG. 1 is manufactured. The housing base 13 and the cover 14 may be welded by heat. Alternatively, the housing base 13 and the cover 14 may be adhered with an adhesive.

Second Embodiment

Figure 10:
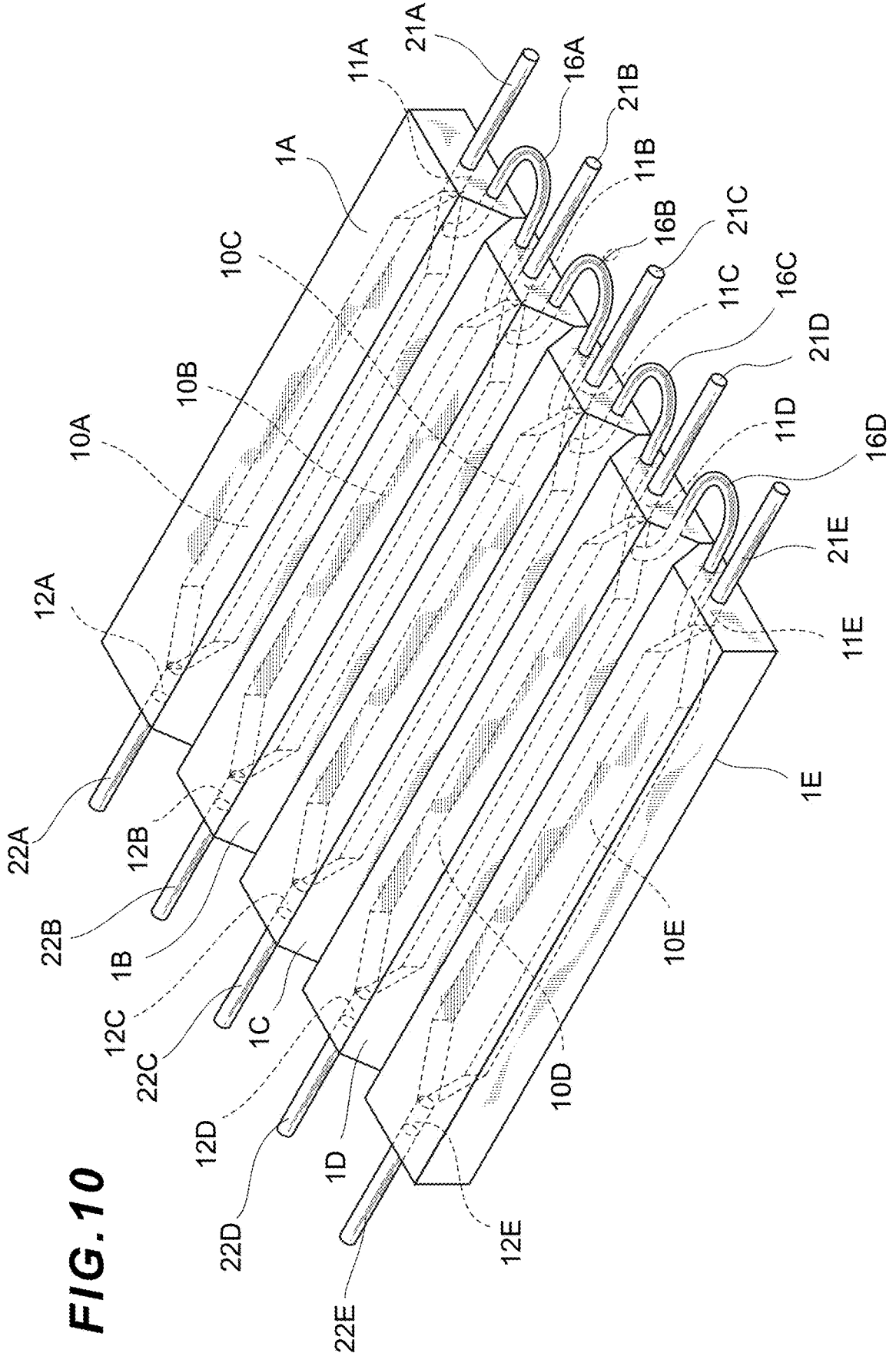
FIG. 10 is a schematic perspective view of a culture vessel according to a second embodiment.

As shown in FIG. 10, a culture vessel according to a second embodiment includes a plurality of housings 1A, 1B, 1C, 1D, and 1E. The plurality of housings 1A, 1B, 1C, 1D, and 1E can be separated from each other. For example, the gaps between the plurality of housings 1A, 1B, 1C, 1D, and 1E each have a thin thickness, and can be broken by human power.

A first connection flow path 21A is connected to a first hole 11A of the housing 1A, and a second connection flow path 22A is connected to a second hole 12A of the housing 1A. A first connection flow path 21B is connected to a first hole 11B of the housing 1B, and a second connection flow path 22B is connected to a second hole 12B of the housing 1B. A first connection flow path 21C is connected to a first hole 11C of the housing 1C, and a second connection flow path 22C is connected to a second hole 12C of the housing 1C. A first connection flow path 21D is connected to a first hole 11D of the housing 1D, and a second connection flow path 22D is connected to a second hole 12D of the housing 1D. A first connection flow path 21E is connected to a first hole 11E of the housing 1E, and a second connection flow path 22E is connected to a second hole 12E of the housing 1E.

An inter-housing flow path 16A that connects a culture chamber 10A of the housing 1A and a culture chamber 10B of the housing 1B is connected between a hole provided in the housing 1A and a hole provided in the housing 1B. An inter-housing flow path 16B that connects the culture chamber 10B of the housing 1B and a culture chamber 10C of the housing 1C is connected between a hole provided in the housing 1B and a hole provided in the housing 1C. An inter-housing flow path 16C that connects the culture chamber 10C of the housing 1C and a culture chamber 10D of the housing 1D is connected between a hole provided in the housing 1C and a hole provided in the housing 1D. An inter-housing flow path 16D that connects the culture chamber 10D of the housing 1D and a culture chamber 10E of the housing 1E is connected between a hole provided in the housing 1D and a hole provided in the housing 1E.

For example, before cells are cultured in the plurality of housings 1A, 1B, 1C, 1D, and 1E, the first connection flow paths 21A to 21E and the second connection flow paths 22A to 22E are blocked.

Figure 11:
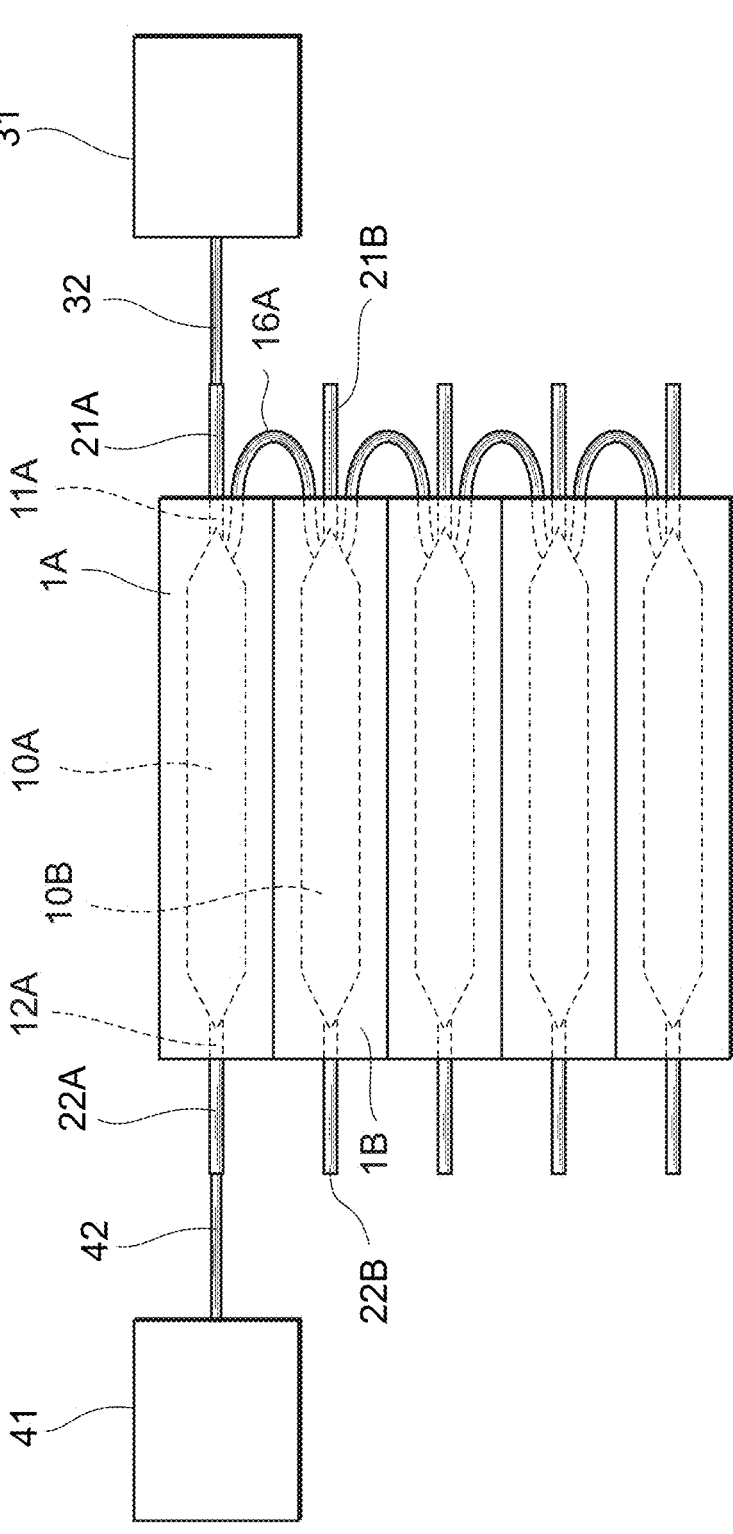
FIG. 11 is a schematic top view of the culture vessel according to the second embodiment.

As shown in FIG. 11, in the case where cells are cultured in the housing 1A, the first connection flow path 32 of the variable volume container 31 containing the solution containing the cells therein is sterilely bonded to the first connection flow path 21A connected to the housing 1A. In addition, the second connection flow path 42 of the expandable variable volume container 41 is sterilely bonded to the second connection flow path 22A connected to the housing 1A.

In the case where the volume of the variable volume container 31 containing the solution containing the cells therein contracts and the volume of the variable volume container 41 which is empty or contains any fluid expands, a gas such as air in the culture chamber 10A of the housing 1A moves into the variable volume container 41 via the second hole 12A, the second connection flow path 22A, and the second connection flow path 42. In addition, the solution containing the cells in the variable volume container 31 moves into the culture chamber 10A of the housing 1A via the first connection flow path 32, the first connection flow path 21A, and the first hole 11A.

It should be noted that, even if the inter-housing flow paths 16A to 16D are not blocked, if the first connection flow paths 21B to 21E and the second connection flow paths 22B to 22E are blocked, the resistance of atmospheric pressure in the culture chamber 10B of the housing 1B can prevent the solution containing the cells from entering the culture chamber 10B of the housing 1B.

Figure 12:
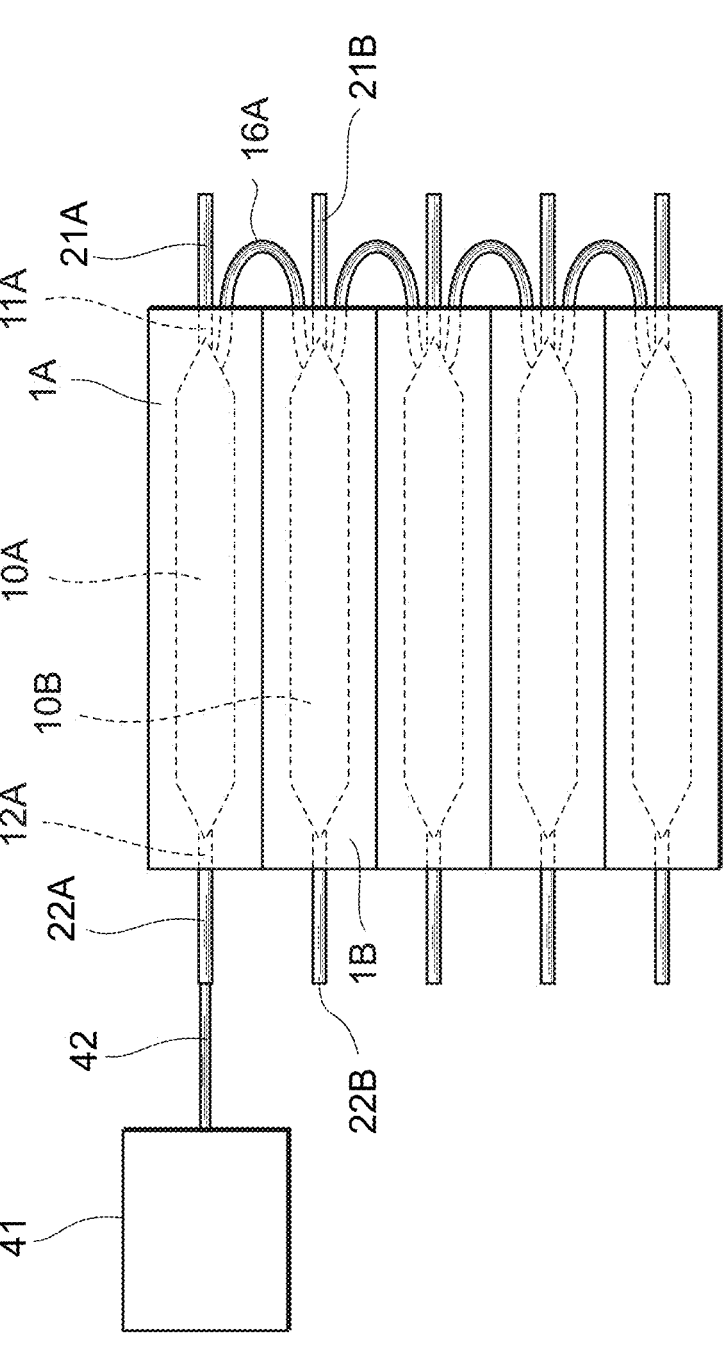
FIG. 12 is a schematic top view of the culture vessel according to the second embodiment.
Figure 13:
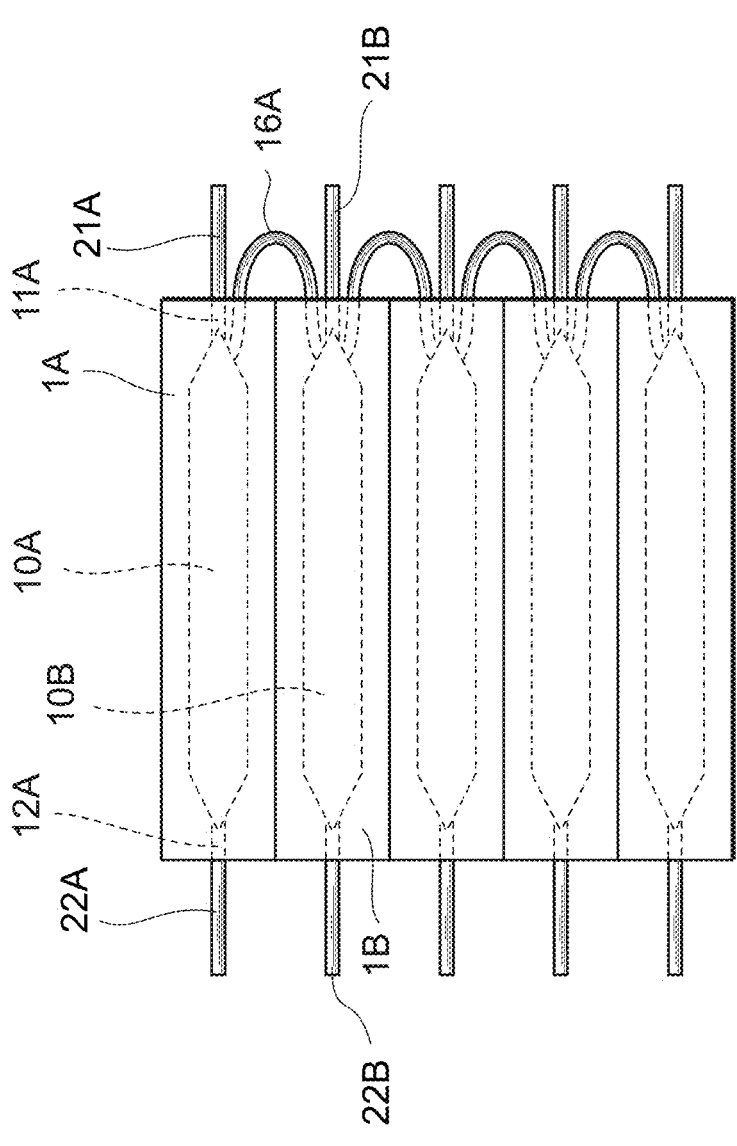
FIG. 13 is a schematic top view of the culture vessel according to the second embodiment.

Then, the first connection flow path 21A may be blocked, and the variable volume container 31 and the first connection flow path 32 may be removed as shown in FIG. 12. Alternatively, the first connection flow path 21A and the second connection flow path 22A may be blocked, and the variable volume container 31, the first connection flow path 32, the variable volume container 41, and the second connection flow path 42 may be removed as shown in FIG. 13. After the variable volume container 31 and the variable volume container 41 are removed, the housing 1A may be placed in a temperature control chamber that can be set to a temperature suitable for cell culture.

Figure 14:
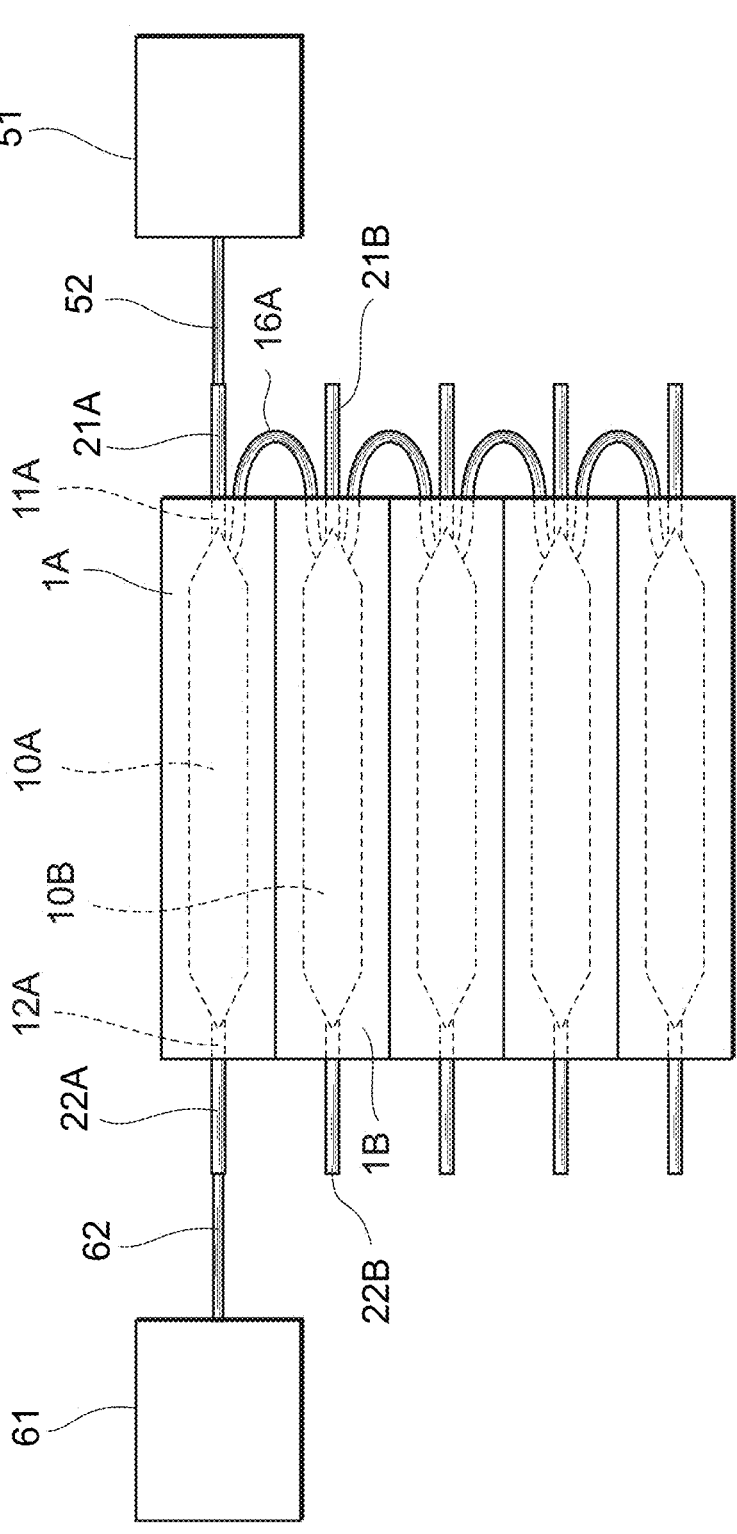
FIG. 14 is a schematic top view of the culture vessel according to the second embodiment.

In the case where the medium in the housing 1A is replaced, as shown in FIG. 14, the first connection flow path 52 of the variable volume container 51 containing the solution containing the medium therein is sterilely bonded to the first connection flow path 21A connected to the housing 1A. In addition, the second connection flow path 62 of the expandable variable volume container 61 is sterilely bonded to the second connection flow path 22A connected to the housing 1A. Here, if the variable volume container 41 is not removed, the connected variable volume container 41 may be used. The variable volume container 51 containing the solution containing the medium may be placed in a temperature control chamber that can be set to a temperature suitable for the medium before it is connected to the housing 1A.

In the case where the volume of the variable volume container 51 containing the medium therein contracts and the volume of the variable volume container 61 which is empty or contains any fluid expands, the medium used in the culture chamber 10A of the housing 1A moves into the variable volume container 61 via the second hole 12A, the second connection flow path 22A, and the second connection flow path 62. In addition, the medium in the variable volume container 51 moves into the culture chamber 10A of the housing 1A via the first connection flow path 52, the first connection flow path 21A, and the first hole 11A.

Then, the first connection flow path 21A may be blocked, and the variable volume container 51 and the first connection flow path 52 may be removed. Alternatively, the first connection flow path 21A and the second connection flow path 22A may be blocked, and the variable volume container 51, the first connection flow path 52, the variable volume container 61, and the second connection flow path 62 may be removed. After the variable volume container 51 and the variable volume container 61 are removed, the housing 1A may be placed in a temperature control chamber that can be set to a temperature suitable for cell culture.

Figure 15:
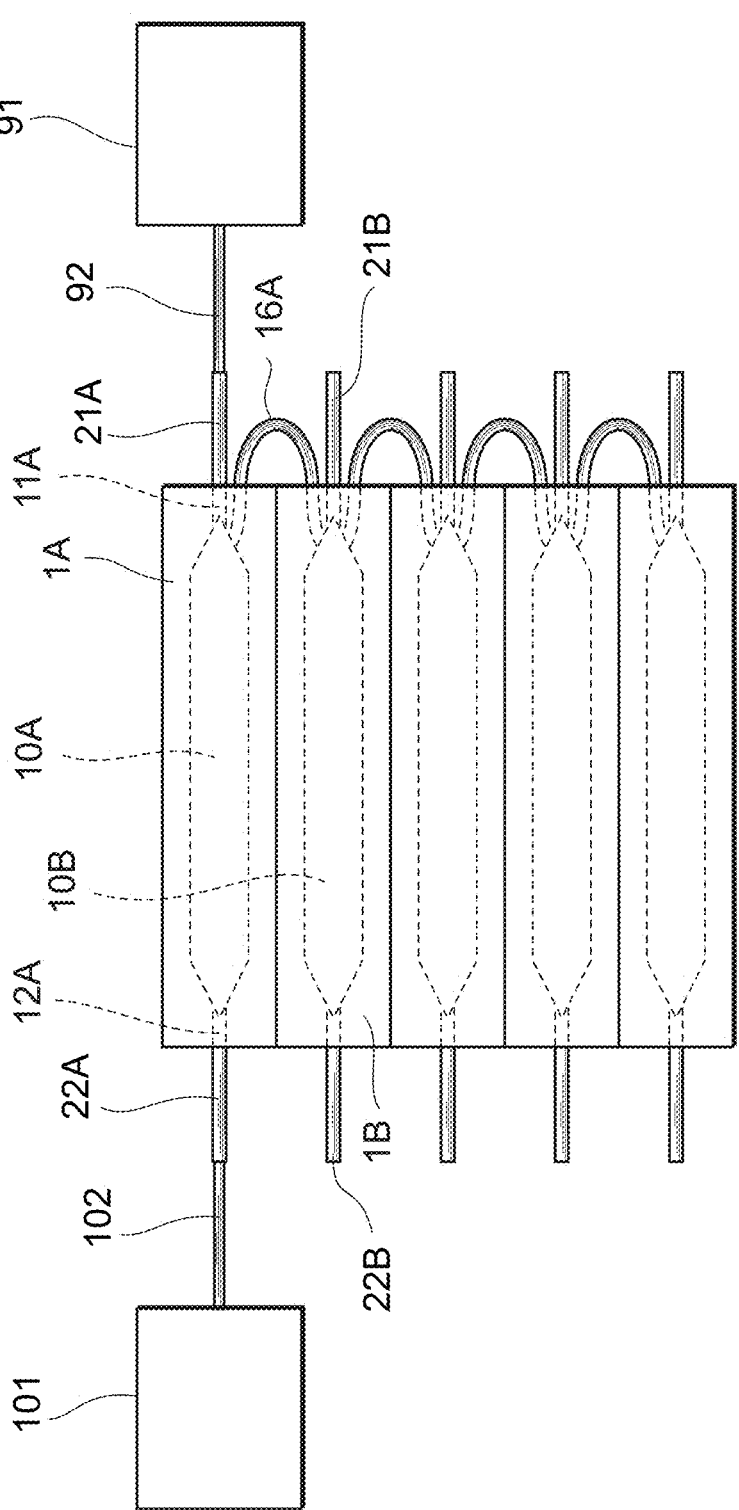
FIG. 15 is a schematic top view of the culture vessel according to the second embodiment.

In the case where the cells in the housing 1A are detached, as shown in FIG. 15, the first connection flow path 92 of the variable volume container 91 containing the dissociation reagent therein is sterilely bonded to the first connection flow path 21A connected to the housing 1A. In addition, the second connection flow path 102 of the expandable variable volume container 101 is sterilely bonded to the second connection flow path 22A connected to the housing 1A. Here, if the variable volume container 41 is not removed, the connected variable volume container 41 may be used. The variable volume container 91 containing the solution containing the dissociation reagent may be placed in a temperature control chamber that can be set to a temperature suitable for the dissociation reagent before it is connected to the housing 1A.

In the case where the volume of the variable volume container 91 containing the dissociation reagent therein contracts and the volume of the variable volume container 101 which is empty or contains any fluid expands, the medium used in the culture chamber 10A of the housing 1A moves into the variable volume container 101 via the second hole 12A, the second connection flow path 22A and the second connection flow path 102. In addition, the dissociation reagent in the variable volume container 91 moves into the culture chamber 10A of the housing 1A via the first connection flow path 92, the first connection flow path 21A, and the first hole 11A.

Figure 16:
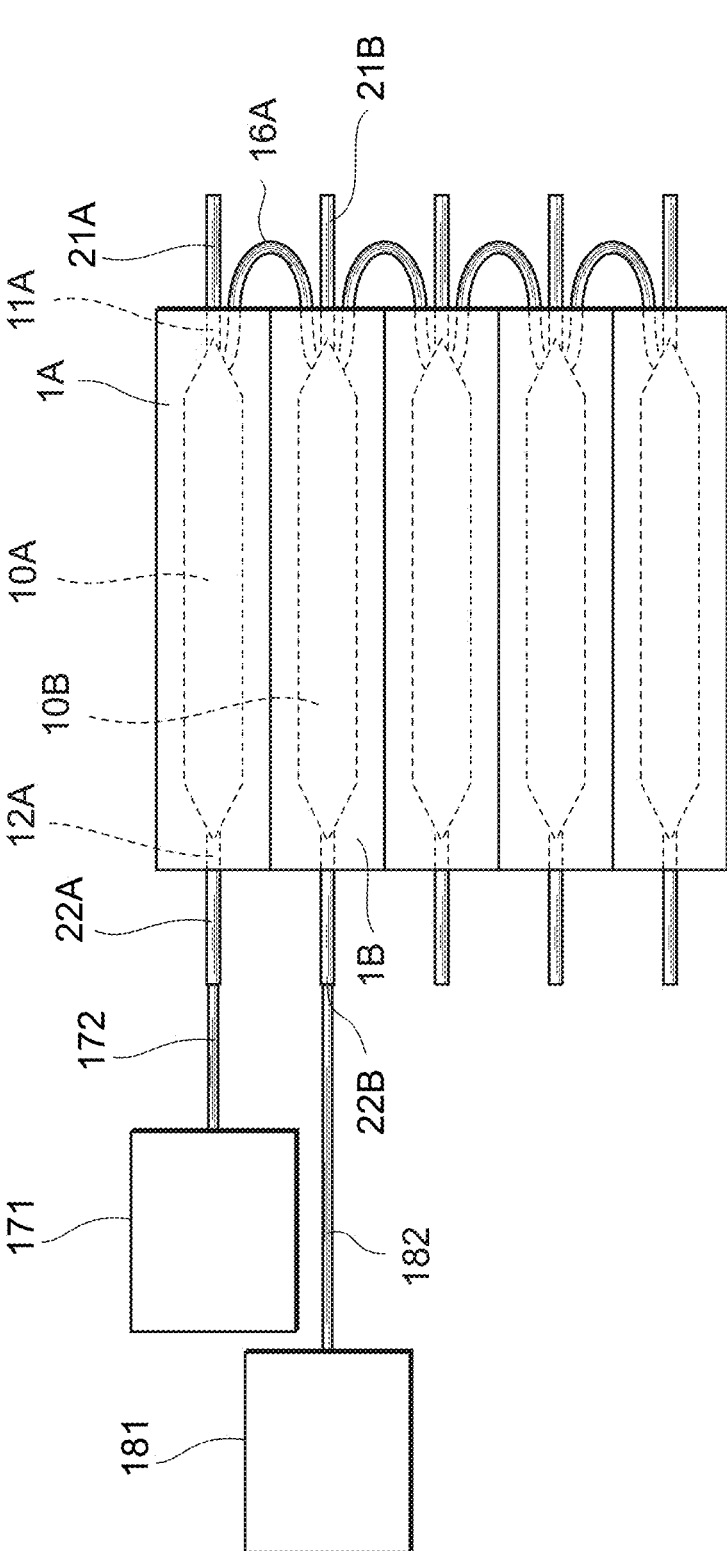
FIG. 16 is a schematic top view of the culture vessel according to the second embodiment.

In the case where the floating cells in the housing 1A are moved into the housing 1B, as shown in FIG. 16, a first connection flow path 172 of a variable volume container 171 containing a solution containing a medium therein is sterilely bonded to the second connection flow path 22A connected to the housing 1A. Here, the first connection flow path 172 of the variable volume container 171 containing the solution containing the medium therein may be sterilely bonded to the first connection flow path 21A connected to the housing 1A. In addition, a second connection flow path 182 of an expandable variable volume container 181 is sterilely bonded to the second connection flow path 22B connected to the housing 1B.

In the case where the volume of the variable volume container 171 containing the medium therein changes and contracts, and the volume of the variable volume container 181 which is empty or contains any fluid changes and expands, a gas in the culture chamber 10B of the housing 1B moves into the variable volume container 181 via the second connection flow path 22B and the second connection flow path 182. In addition, the cells suspended in the culture chamber 10A of the housing 1A move into the culture chamber 10B of the housing 1B via the inter-housing flow path 16A.

Figure 17:
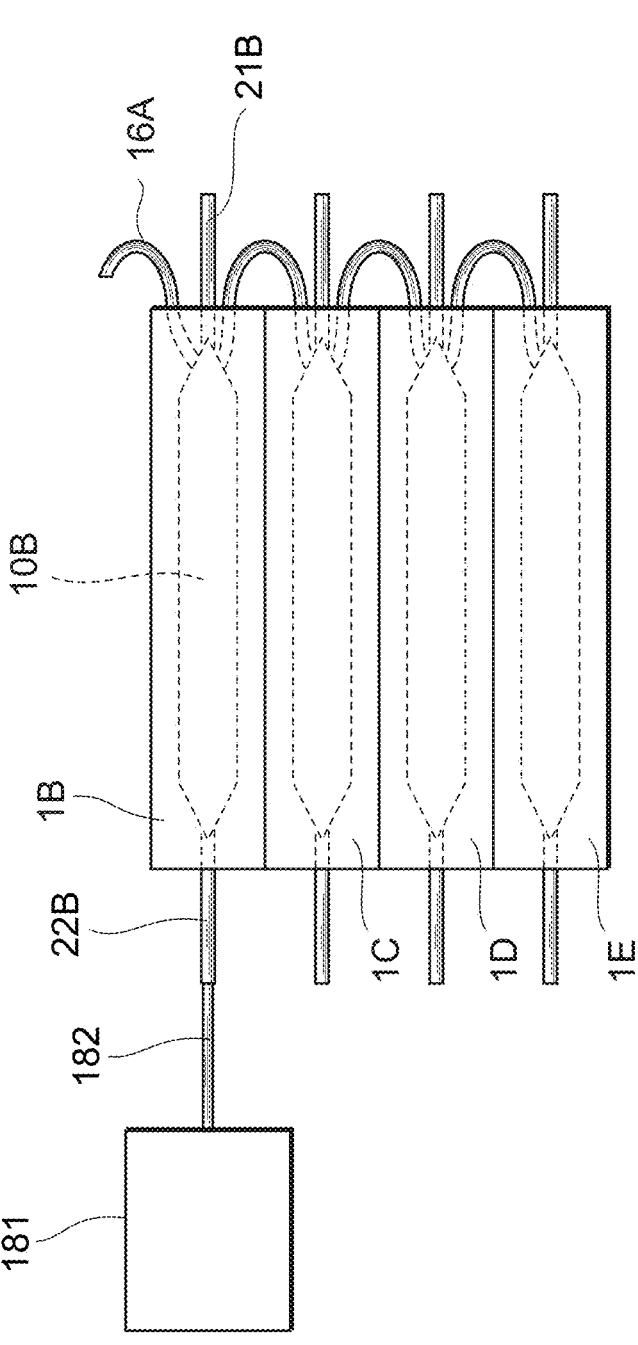
FIG. 17 is a schematic top view of the culture vessel according to the second embodiment.
Figure 18:
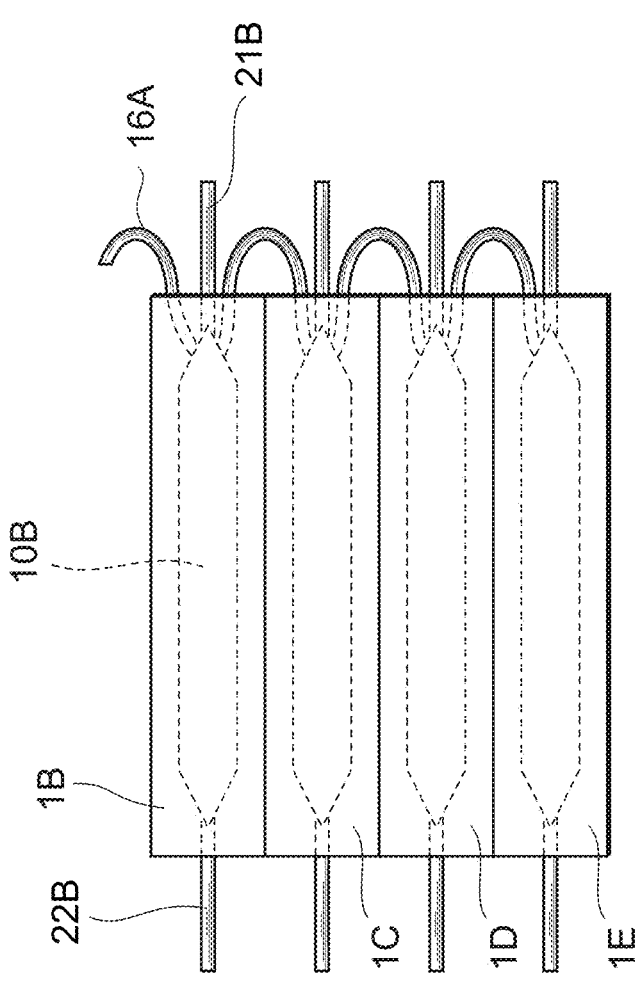
FIG. 18 is a schematic top view of the culture vessel according to the second embodiment.

Then, as shown in FIG. 17, the inter-housing flow path 16A is blocked, and additionally, the inter-housing flow path 16A may be cut on the side of the housing 1A from the blocked part of the inter-housing flow path 16A, and the housing 1A may be separated from the housing 1B. In addition, as shown in FIG. 18, the variable volume container 181 and the second connection flow path 182 may be removed.

Hereinafter, as in the housing 1A, the cells in the housing 1B may be cultured, the medium may be replaced, and additionally, the cells may be moved into the housing 1C. In addition, the cells may be moved into the housings 1C, 1D, and 1E.

Figure 19:
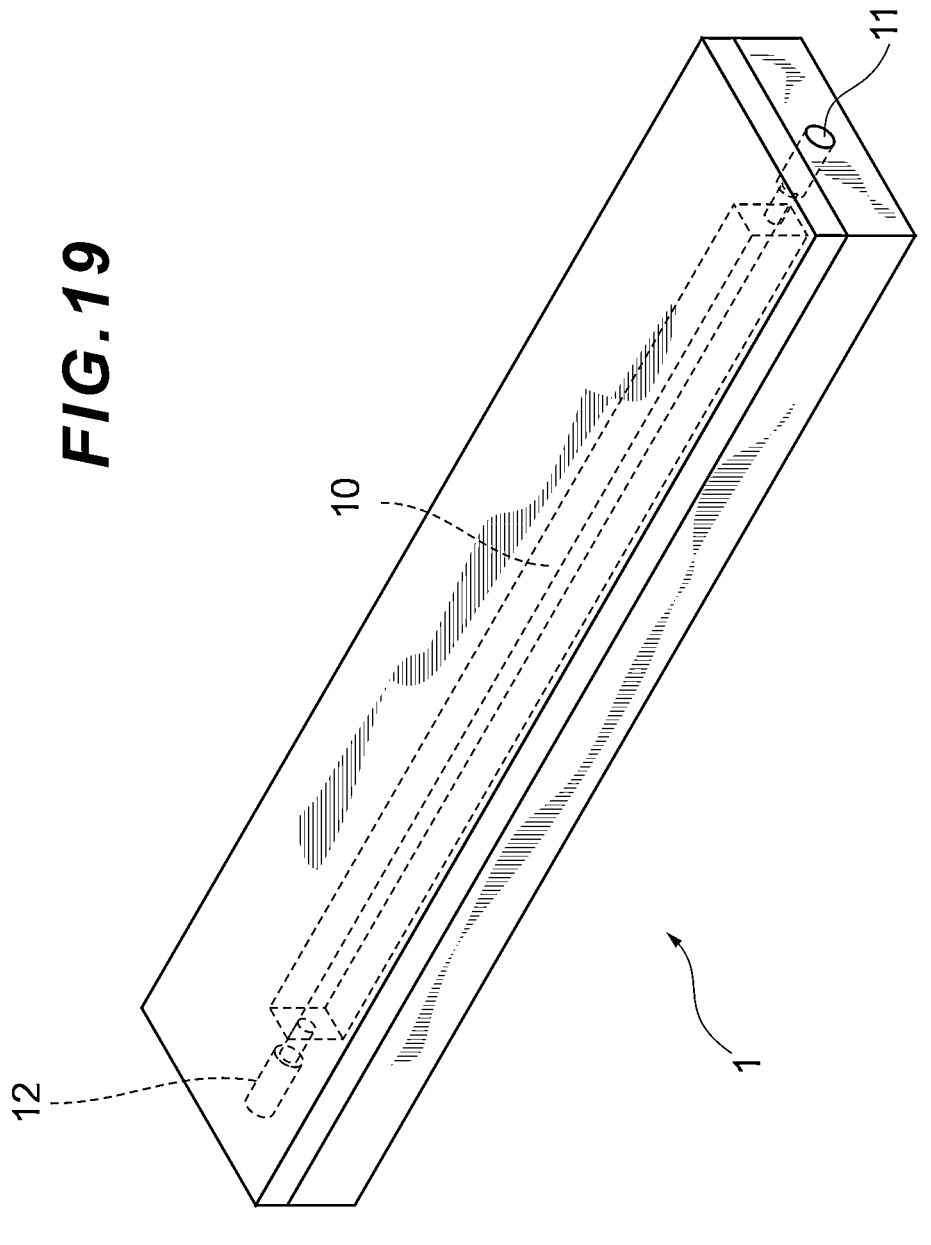
FIG. 19 is a schematic perspective view of a culture vessel according to another embodiment.
Figure 20:
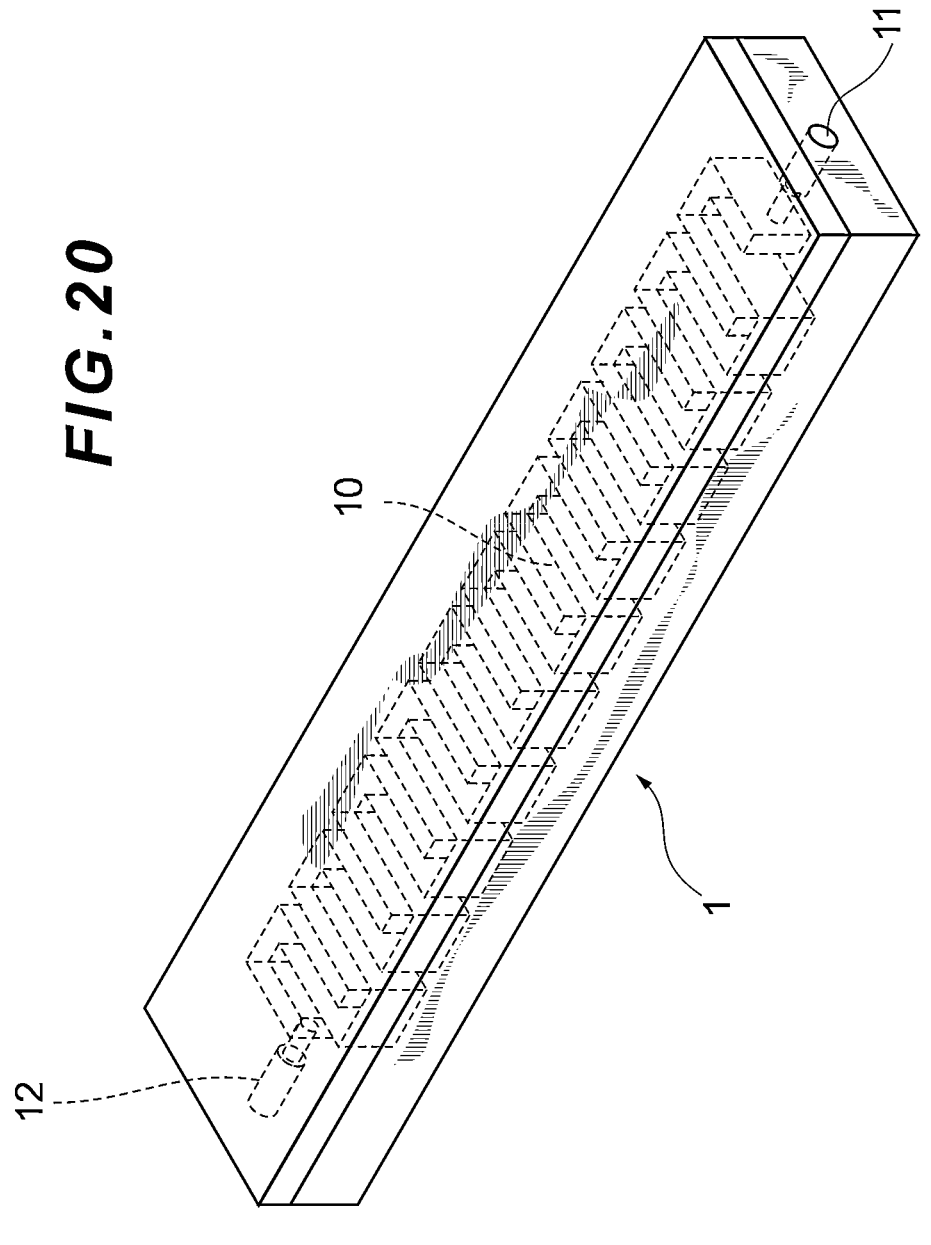
FIG. 20 is a schematic perspective view of a culture vessel according to another embodiment.
Figure 23C:
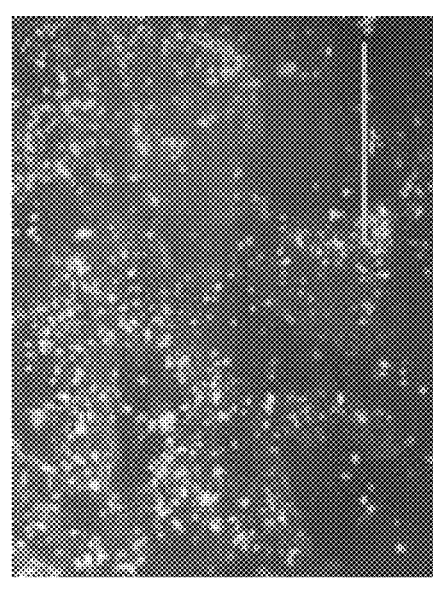
FIG. 23A to FIG. 23D show microscope images of cells according to Example 1.
Figure 23D:
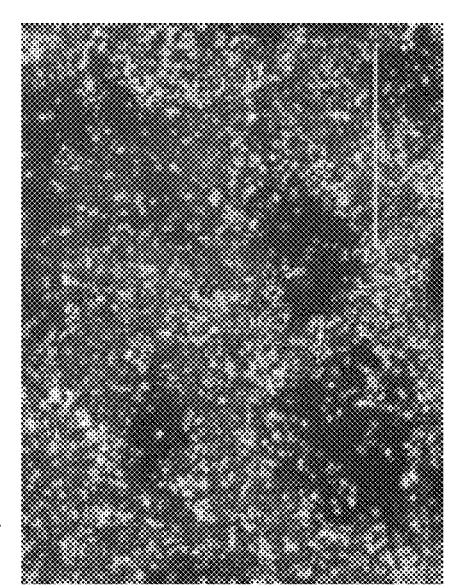
Figure 23A:
Figure 23B:
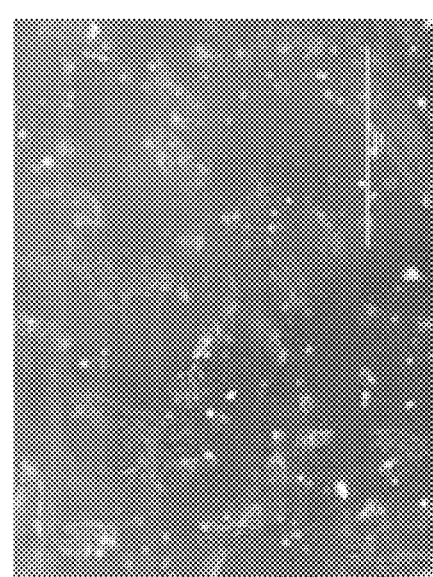

While the present invention has been described above with reference to the embodiments, the descriptions and drawings that form some of the disclosure should not be understood as limiting the invention. Those skilled in the art can clearly understand various alternative embodiments, embodiments and operated techniques from this disclosure. For example, the culture chamber 10 shown in FIG. 1 has a hexagonal shape when viewed from above, but the shape is not particularly limited. For example, as shown in FIG. 19, the culture chamber 10 may have a rectangular shape when viewed from above. Alternatively, as shown in FIG. 20, the culture chamber 10 may have a polygonal line that continuously and alternately changes its direction when viewed from above.

In addition, as shown in FIG. 21A to FIG. 21C, a hollow fiber membrane 110 may be disposed in the culture chamber 10. Both ends of the hollow fiber membrane 110 are connected to the first hole 11 and the second hole 12 of the housing 1. In this case, a third hole 111 and a fourth hole 112 may be provided in the housing 1. For example, a variable volume container is connected to the first hole 11, the second hole 12, the third hole 111 and the fourth hole 112 of the housing 1. For example, a solution containing cells is introduced into the hollow fiber membrane 110 from the first hole 11, and the solution containing the cells in the hollow fiber membrane 110 is discharged from the second hole 12. In this case, a solution containing no cells is introduced from the third hole 111 to the outside of the hollow fiber membrane 110 of the culture chamber 10, and the solution containing no cells outside the hollow fiber membrane 110 is discharged from the fourth hole 112. Alternatively, a solution containing no cells is introduced from the first hole 11 into the hollow fiber membrane 110, and the solution containing no cells in the hollow fiber membrane 110 is discharged from the second hole 12. In this case, a solution containing cells is introduced from the third hole 111 to the outside of the hollow fiber membrane 110 of the culture chamber 10, and the solution containing no cells outside the hollow fiber membrane 110 is discharged from the fourth hole 112.

Figures 22A, 22B, 22C:
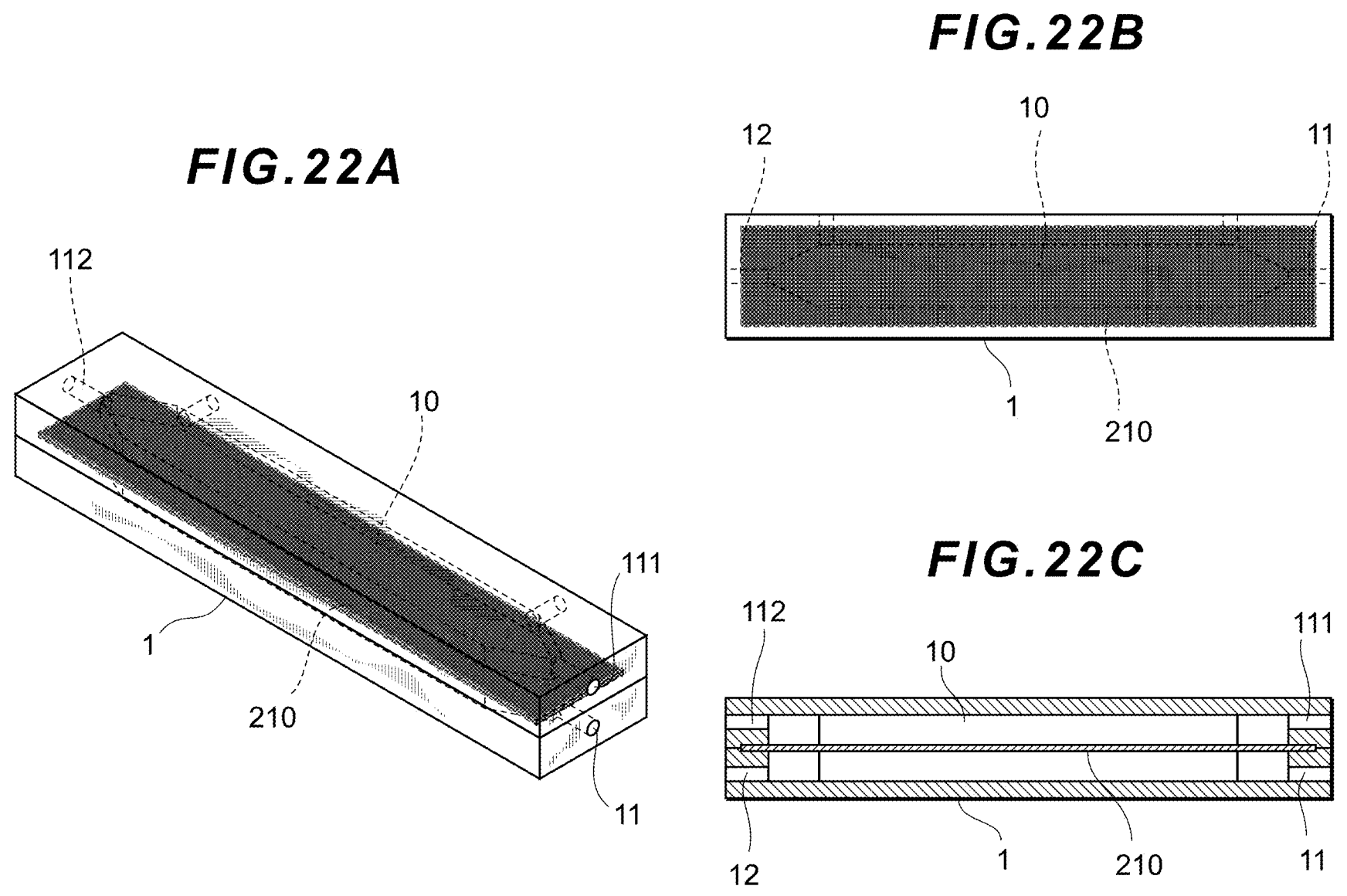

In addition, as shown in FIG. 22A to FIG. 22C, a semipermeable membrane 210 may be disposed in the culture chamber 10, and the culture chamber 10 may be divided by the semipermeable membrane 210. In this case, the first hole 11 and the second hole 12 that communicate with one side of the culture chamber 10 divided by the semipermeable membrane 210 may be provided in the housing 1, and the third hole 111 and the fourth hole 112 that communicate with the other side of the culture chamber 10 divided by the semipermeable membrane 210 may be provided. For example, a solution containing cells is introduced into one side of the culture chamber 10 divided by the semipermeable membrane 210 from the first hole 11, and the solution containing the cells in one side of the culture chamber 10 is discharged from the second hole 12. In this case, a solution containing no cells is introduced into the other side of the culture chamber 10 divided by the semipermeable membrane 210 from the third hole 111, and the solution containing no cells in the other side of the culture chamber 10 is discharged from the fourth hole 112. Alternatively, a solution containing no cells is introduced into one side of the culture chamber 10 divided by the semipermeable membrane 210 from the first hole 11, and the solution containing no cells in one side of the culture chamber 10 is discharged from the second hole 12. In this case, a solution containing cells is introduced into the other side of the culture chamber 10 divided by the semipermeable membrane 210 from the third hole 111, and the solution containing the cells in the other side of the culture chamber 10 is discharged from the fourth hole 112. As described above, it should be understood that the present invention includes various embodiments not described here and the like.

Example 1: Culture of iPS Cells

A housing as shown in FIG. 2B was prepared, and the inside was coated with a laminin 511E8 fragment. Next, a first connection flow path of a variable volume container containing a medium in which iPS cells were suspended was sterilely bonded to a first connection flow path of the housing. A second connection flow path of an empty variable volume container was sterilely bonded to a second connection flow path of the housing. A gas in the housing was discharged into the empty variable volume container, the medium in which the iPS cells were suspended was injected into the housing from the variable volume container containing the medium in which the iPS cells were suspended, and $1 \times 10^5$ iPS cells were seeded in the housing 1. Regarding the medium, a medium for stem cells (StemFit, registered trademark, Ajinomoto) containing a 10 μmol/L ROCK inhibitor was used. After the cells were seeded, each of the first connection flow path and the second connection flow path was blocked by thermocompression bonding to close the inside of the housing, the housing 1 was disposed in a thermostatic chamber at 37° C., and the iPS cells in the housing were cultured.

Then, the medium in the housing was replaced once every two days. When the medium was replaced, a first connection flow path of a variable volume container containing a fresh medium for stem cells was sterilely bonded to the first connection flow path of the housing, and a second connection flow path of an empty variable volume container was sterilely bonded to the second connection flow path of the housing. The medium used in the housing was discharged into the variable volume container, and the fresh medium for stem cells was injected into the housing 1 from the variable volume container 31 containing the fresh medium for stem cells. After the medium was replaced, each of the first connection flow path and the second connection flow path was blocked by thermocompression bonding, the inside of the housing was closed, and the housing was disposed in a thermostatic chamber at 37° C. As a result, as shown in FIG. 23A to FIG. 23D, the iPS cells proliferated in the housing 1.

Example 2: Preparation of Induced Cells

Peripheral blood mononuclear cells were seeded in wells of a microplate at $1 \times 10^3$ cells/well to $1 \times 10^5$ cells/well, the microplate was placed in a thermostatic chamber at 37° C., and the cells were cultured. On the 6th day after the culture started, the medium in the well was replaced using a medium for blood cells containing Sendai viruses that can express reprogramming factors OSKM (OCT3/4, SOX2, KLF4, c-MYC).

Then, a housing as shown in FIG. 2B, which is a housing in which the inside was coated with a laminin 511E8 fragment, was prepared, and a first connection flow path of a variable volume container containing a medium in which the cells infected with Sendai viruses were suspended was sterilely bonded to a first connection flow path of the housing, and a second connection flow path of an empty variable volume container was sterilely bonded to a second connection flow path of the housing. A gas in the housing was discharged into the empty variable volume container, the cells infected with Sendai virus were injected into the housing from the variable volume container containing cells infected with Sendai virus, and the cells infected with Sendai viruses were seeded in the housing. After the cells were seeded, each of the first connection flow path and the second connection flow path was blocked by thermocompression bonding to close the inside of the housing, the housing was placed in a thermostatic chamber at 34° C., and the cells in the housing were cultured.

Figure 24B:
FIG. 24A and FIG. 24B show microscope images of cells according to Example 2.
Figure 24A:
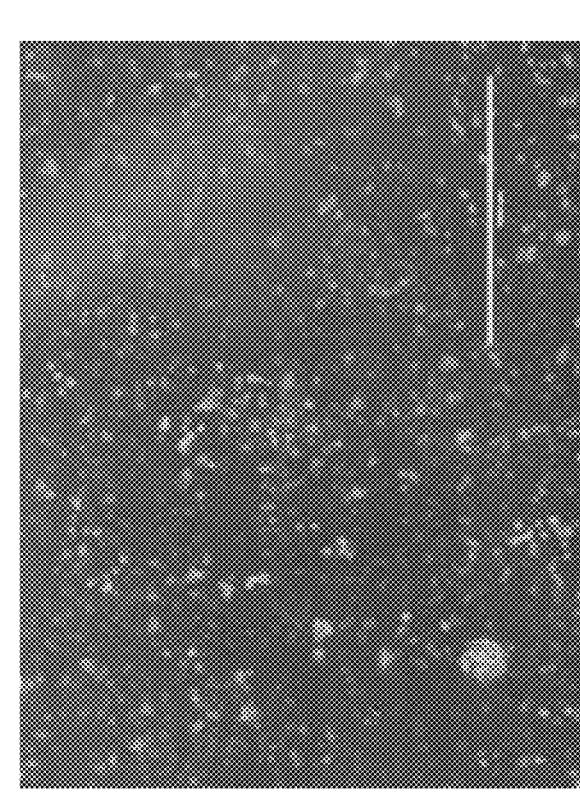

The medium in the housing was replaced once every two days after the cells were infected with Sendai viruses. When the medium was replaced, a first connection flow path of a variable volume container containing a fresh medium for stem cells was sterilely bonded to the first connection flow path of the housing, and a second connection flow path of an empty variable volume container was sterilely bonded to the second connection flow path of the housing. The medium used in the housing was discharged into the empty variable volume container and the fresh medium for stem cells was injected into the housing from the variable volume container containing the fresh medium for stem cells. After the medium was replaced, each of the first connection flow path and the second connection flow path was blocked by thermocompression bonding to close the inside of the housing, and the housing was placed in a thermostatic chamber. The temperature of the thermostatic chamber was set to 37° C. on the 5th day after the cells were infected with Sendai viruses, and set to 38° C. to 40° C. after the 7th day. As a result, as shown in FIG. 24A and FIG. 24B, colonies of iPS cell-like cells were formed in the housing 1 on the 10th to 20th days after the cells were infected with Sendai viruses.

Example 3: Preparation of Induced Cells

A housing as shown in FIG. 2B was prepared, and the inside was coated with a laminin 511E8 fragment. Next, a first connection flow path of a variable volume container containing a medium in which peripheral blood mononuclear cells were suspended was sterilely bonded to a first connection flow path of the housing, and a second connection flow path of an empty variable volume container was sterilely bonded to a second connection flow path of the housing. Regarding the medium, a medium for blood cells was used. A gas in the housing was discharged into the empty variable volume container, the medium in which the peripheral blood mononuclear cells were suspended was injected into the housing from the variable volume container 31 containing the medium in which the peripheral blood mononuclear cells were suspended, and $1 \times 10^3$ to $1 \times 10^5$ peripheral blood mononuclear cells were seeded in the housing. After the cells were seeded, each of the first connection flow path and the second connection flow path was blocked by thermocompression bonding to close the inside of the housing, the housing was placed in a thermostatic chamber at 37° C., and the cells in the housing were cultured.

The medium in the housing was replaced once every two or three days. When the medium was replaced, a first connection flow path of a variable volume container containing a fresh medium for blood cells was sterilely bonded to the first connection flow path of the housing, and a second connection flow path of an empty variable volume container was sterilely bonded to the second connection flow path of the housing. The medium used in the housing was discharged into the empty variable volume container, and the fresh medium for blood cells was injected into the housing from the variable volume container containing the fresh medium for blood cells. After the medium was replaced, each of the first connection flow path and the second connection flow path was blocked by thermocompression bonding, the inside of the housing was closed, and the housing was placed in a thermostatic chamber at 37° C.

On the 6th day after cell culture in the housing started, the medium in the housing was replaced using a medium for blood cells containing Sendai viruses that can express reprogramming factors OSKM (OCT3/4, SOX2, KLF4, c-MYC). In this case, a first connection flow path of a variable volume container containing a medium for blood cells containing Sendai viruses was sterilely bonded to the first connection flow path of the housing, and a second connection flow path of an empty variable volume container was sterilely bonded to the second connection flow path of the housing. The medium used in the housing was discharged into the empty variable volume container, and the medium for blood cells containing the Sendai viruses was injected into the housing from the variable volume container containing the medium for blood cells containing the Sendai viruses. After the medium was replaced, each of the first connection flow path and the second connection flow path was blocked by thermocompression bonding to close the inside of the housing, and the housing was placed in a thermostatic chamber at 34° C.

Figures 25A, 25B:
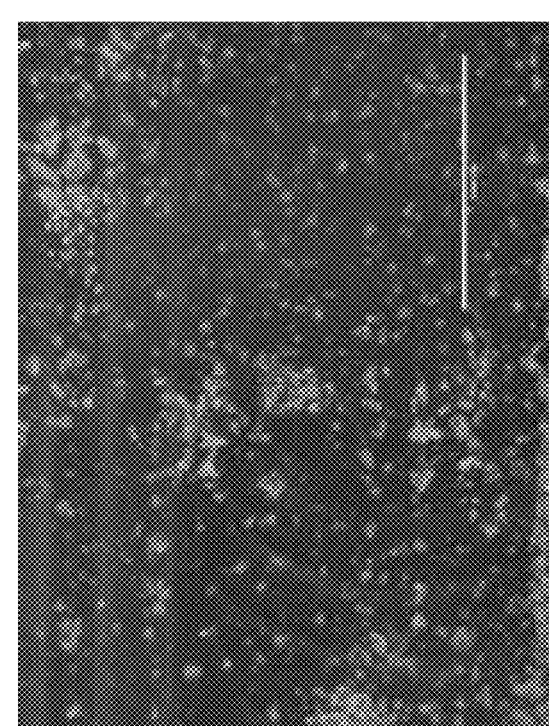
FIG. 25A and FIG. 25B show microscope images of cells according to Example 3.

The medium in the housing was replaced once every two days after the cells were infected with Sendai viruses. When the medium was replaced, a first connection flow path of a variable volume container containing a fresh medium for stem cells was sterilely bonded to the first connection flow path of the housing, and a second connection flow path of an empty variable volume container was sterilely bonded to the second connection flow path of the housing. The medium used in the housing was discharged into the empty variable volume container and the fresh medium for stem cells was injected into the housing from the variable volume container containing the fresh medium for stem cells. After the medium was replaced, each of the first connection flow path and the second connection flow path was blocked by thermocompression bonding to close the inside of the housing, and the housing was placed in a thermostatic chamber. The temperature of the thermostatic chamber was set to 37° C. on the 5th day after the cells were infected with Sendai viruses, and set to 38° C. to 40° C. after the 7th day. As a result, as shown in FIG. 25A and FIG. 25B, colonies of iPS cell-like cells were formed in the housing 1 on the 10th to 20th days after the cells were infected with Sendai viruses.

After formation of colonies of iPS cell-like cells was confirmed, a first connection flow path of a variable volume container containing a cell dissociation reagent (TrypLE Select, registered trademark, ThermoFisher SCIENTIFIC) at 37° C. was sterilely bonded to the first connection flow path of the housing as shown in FIG. 2B, and a second connection flow path of an empty variable volume container was sterilely bonded to the second connection flow path of the housing. The medium in the housing was discharged into the empty variable volume container, and the cell dissociation reagent was injected into the housing from the variable volume container containing the cell dissociation reagent. Then, the housing was placed in a thermostatic chamber at 37° C. for 5 minutes to 10 minutes. In addition, the cell dissociation reagent used in the housing was discharged into a variable volume container, and a fresh cell dissociation reagent was injected into the housing. Then, each of the first connection flow path and the second connection flow path was blocked by thermocompression bonding to close the inside of the housing, and the housing was placed in a thermostatic chamber at 37° C. for 5 minutes to 10 minutes.

Next, a first connection flow path of a variable volume container containing a medium for stem cells at 37° C. was sterilely bonded to the first connection flow path of the housing, and a second connection flow path of an empty variable volume container was sterilely bonded to the second connection flow path of the housing. The cell dissociation reagent in the housing was discharged into the empty variable volume container, and the medium for stem cells in the housing was injected from the variable volume container containing the medium for stem cells. Then, each of the first connection flow path and the second connection flow path was blocked by thermocompression bonding to close the inside of the housing. In addition, the housing was stirred, and all cells were removed from the housing.

A first connection flow path of a variable volume container containing a gas was sterilely bonded to the first connection flow path of the housing, and a second connection flow path of a variable volume container was sterilely bonded to the second connection flow path of the housing. The medium in which the cells in the housing were suspended were collected in the empty variable volume container, and a gas was injected into the housing from the variable volume container containing the gas.

Figure 26B:
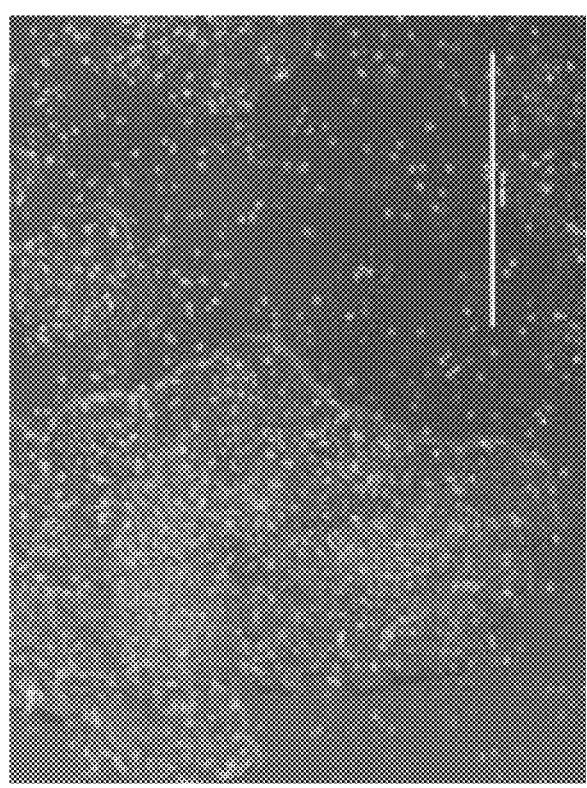
FIG. 26A and FIG. 26B show microscope images of cells according to Example 3.
Figure 26A:
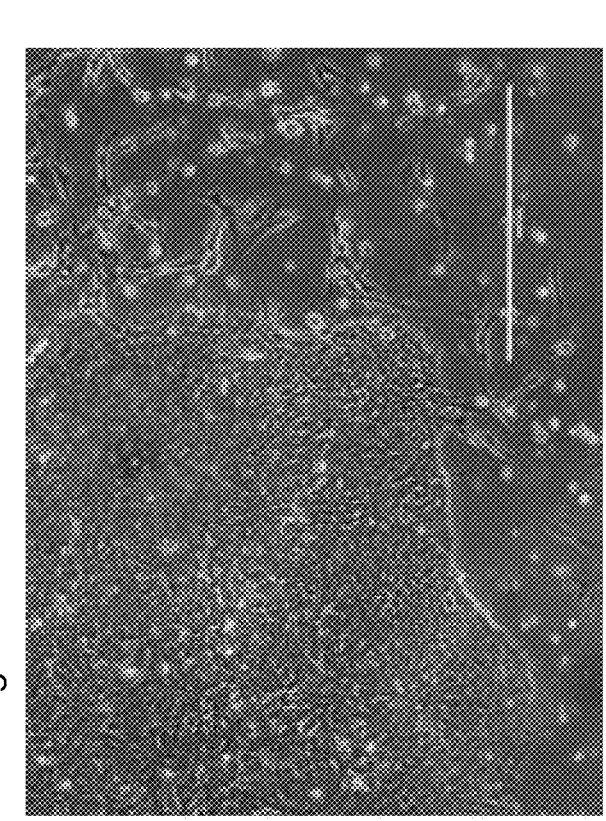

Among the collected cells, $1 \times 10^3$ to $1 \times 10^5$ cells were seeded and passaged using a medium for stem cells in a housing in which the inside was coated with a laminin 511E8 fragment. During the passage, the collected cells were seeded in the housing without distinction without colony picking. Seeding was performed in the same procedure as above. After the passage, the housing was disposed in a thermostatic chamber at 37° C., and the cells in the housing were cultured. Whenever colonies were formed in the housing, passage was performed a total of three times in the same procedure as above. FIG. 26A shows an image of colonies of iPS cell-like cells formed after passage was performed once, and FIG. 26B shows an image of colonies of iPS cell-like cells formed after passage was performed two times. In addition, FIG. 27A to FIG. 27D shows fluorescence microscope images of iPS cell-like cells stained using a Hoechst reagent, an anti-NANOG antibody, and an anti-OCT3/4 antibody. It was confirmed that the cells were NANOG positive and OCT3/4 positive.

Figure 28:
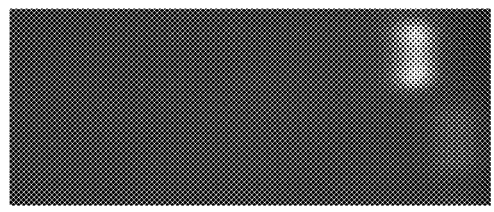
FIG. 28 is an image showing PCR analysis results according to Example 3.

After the cells were passaged three times, RNA was extracted from the cells. cDNA was synthesized from the extracted RNA, and inclusion of Sendai virus-derived cDNA was analyzed by PCR. As a result, as shown in FIG. 28, it was shown that no Sendai viruses remained in the cells.

Example 4: Preparation of GFP-expressing Cells

A housing as shown in FIG. 2B was prepared, and the inside was coated with a laminin 511E8 fragment. Next, a first connection flow path of a variable volume container containing a medium in which fibroblasts were suspended was sterilely bonded to a first connection flow path of the housing, and a second connection flow path of an empty variable volume container was sterilely bonded to a second connection flow path of the housing. Regarding the medium, a medium for fibroblasts was used. A gas in the housing was discharged into the empty variable volume container, the medium in which the fibroblasts were suspended was injected into the housing from the variable volume container containing the medium in which the fibroblasts were suspended, and $1\times10^4$ to $1\times10^5$ fibroblasts were seeded in the housing. After the cells were seeded, each of the first connection flow path and the second connection flow path was blocked by thermocompression bonding to close the inside of the housing, the housing was placed in a thermostatic chamber at 37° C., and the cells in the housing were cultured.

Figures 29A, 29B:
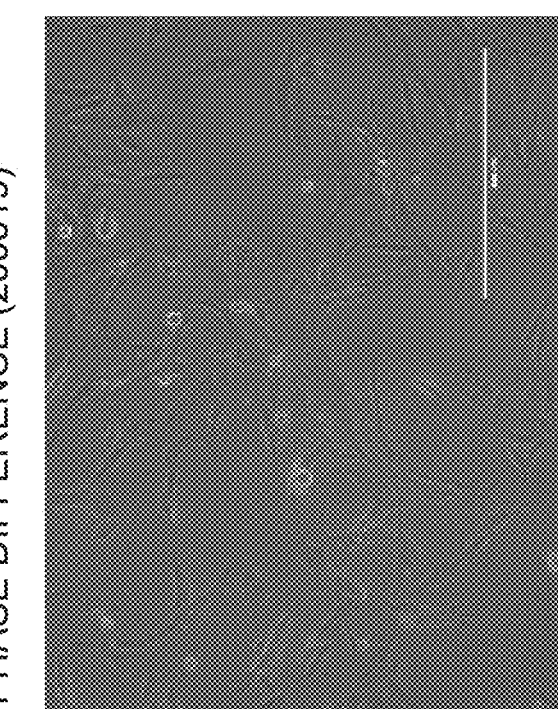
FIG. 29A and FIG. 29B show microscope images of cells according to Example 4.
Figure 31B:
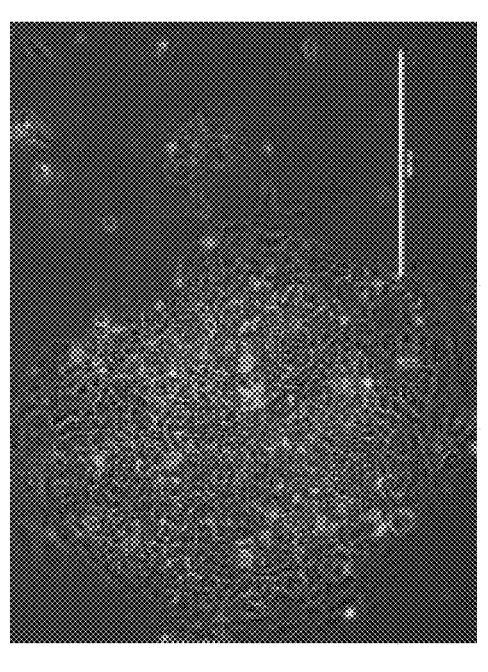
FIG. 31A to FIG. 31D show microscope images of cells according to Example 5.
Figure 31D:
Figure 31A:
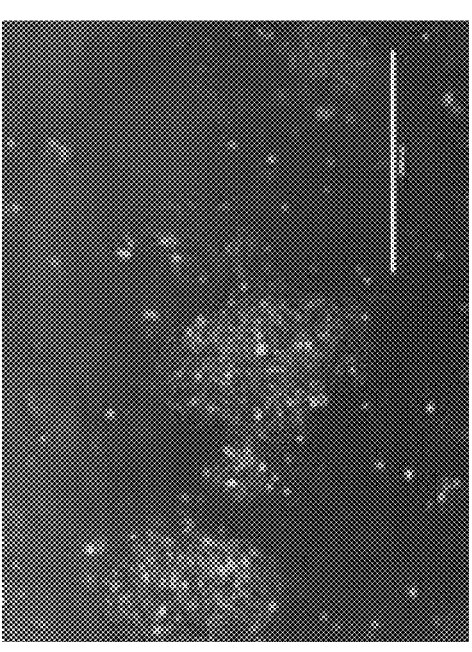
Figure 31C:
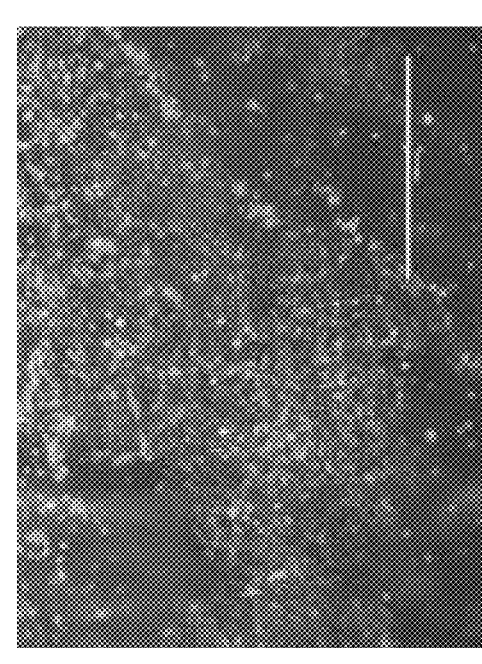

The next day, a first connection flow path of a variable volume container containing a transfection medium containing a mixture of a transfection reagent and RNA encoding a green fluorescent protein (GFP) was sterilely bonded to the first connection flow path of the housing, and a second connection flow path of an empty variable volume container was sterilely bonded to the second connection flow path of the housing. The medium used in the housing was discharged into the empty variable volume container, and the transfection medium was injected into the housing from the variable volume container containing the transfection medium. Then, each of the first connection flow path and the second connection flow path was blocked by thermocompression bonding to close the inside of the housing, the housing was placed in a thermostatic chamber at 37° C., and the cells in the housing were cultured. The next day, when the cells in the housing were observed under a fluorescence microscope, as shown in FIG. 29A and FIG. 29B, it was observed that GFP was expressed.

Example 5: Preparation of Induced Cells

A housing as shown in FIG. 2B was prepared, and the inside was coated with a laminin 511E8 fragment. Next, a first connection flow path of a variable volume container containing a medium in which fibroblasts were suspended was sterilely bonded to a first connection flow path of the housing, and a second connection flow path of an empty variable volume container was sterilely bonded to the second connection flow path of the housing. A gas in the housing was discharged into the empty variable volume container, the medium in which the fibroblasts were suspended was injected into the housing from the variable volume container containing the medium in which the fibroblasts were suspended, and $1\times10^4$ to $1\times10^5$ fibroblasts were seeded in the housing. Regarding the medium, a medium for fibroblasts was used. After the cells were seeded, each of the first connection flow path and the second connection flow path was blocked by thermocompression bonding to close the inside of the housing, the housing was placed in a thermostatic chamber at 37° C., and the cells in the housing were cultured.

The next day, a first connection flow path of a variable volume container containing a transfection medium containing a mixture of a transfection reagent and RNA encoding reprogramming factors OSKM (OCT3/4, SOX2, KLF4, c-MYC) was sterilely bonded to the first connection flow path of the housing 1, and a second connection flow path of an empty variable volume container was sterilely bonded to the second connection flow path of the housing. The medium used in the housing was discharged into the empty variable volume container, and the transfection medium was injected into the housing from the variable volume container containing the transfection medium. Then, each of the first connection flow path and the second connection flow path was blocked by thermocompression bonding to close the inside of the housing, and the housing was placed in a thermostatic chamber at 37° C. For the next 10 days, transfection was performed once a day in the same procedure.

FIG. 30A to FIG. 30D shows microscope images of the cells on the 1st, 4th, 7th and 10th days after the cells were seeded in the housing. As the days progressed, the process of cells changing to iPS cells was confirmed.

On the 11th day after the cells were seeded, the medium in the housing was changed from the medium for fibroblasts to the medium for stem cells. When the medium was replaced, a first connection flow path of a variable volume container containing a fresh medium for stem cells was sterilely bonded to the first connection flow path of the housing, and a second connection flow path of an empty variable volume container was sterilely bonded to the second connection flow path of the housing. The medium used in the housing was discharged into the empty variable volume container, and the medium for stem cells was injected into the housing from the variable volume container 31 containing the medium for stem cells. After the medium was replaced, each of the first connection flow path and the second connection flow path was blocked by thermocompression bonding, the inside of the housing was closed, and the housing was placed in a thermostatic chamber at 37° C. On the 13th day after the cells were seeded, as shown in FIG. 31A to FIG. 31D, iPS cell-like cells in the housing were confirmed. The images of FIG. 31A to FIG. 31D were obtained by imaging four different parts in the housing.

Figure 32B:
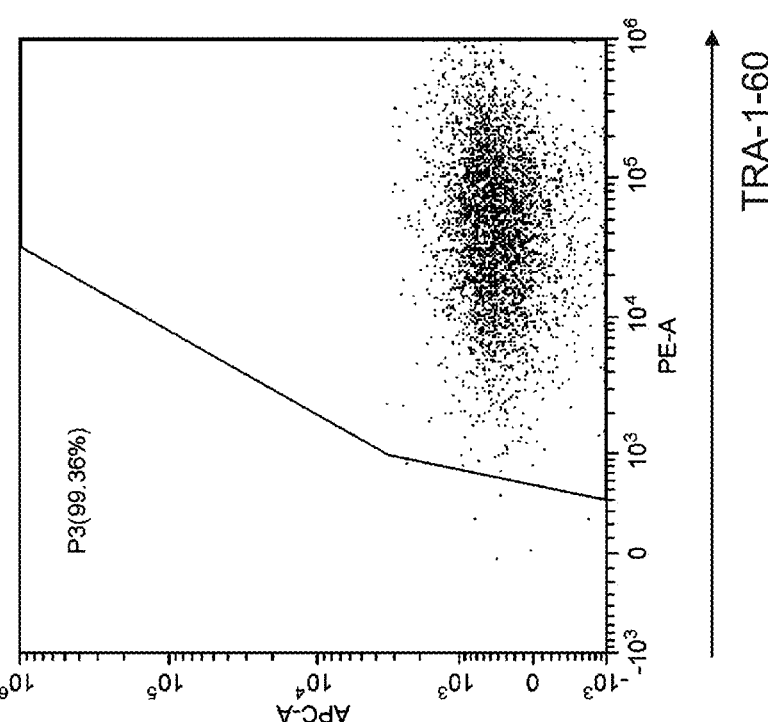
FIG. 32A and FIG. 32B show histograms showing the results of flow cytometry according to Example 5.
Figure 32A:
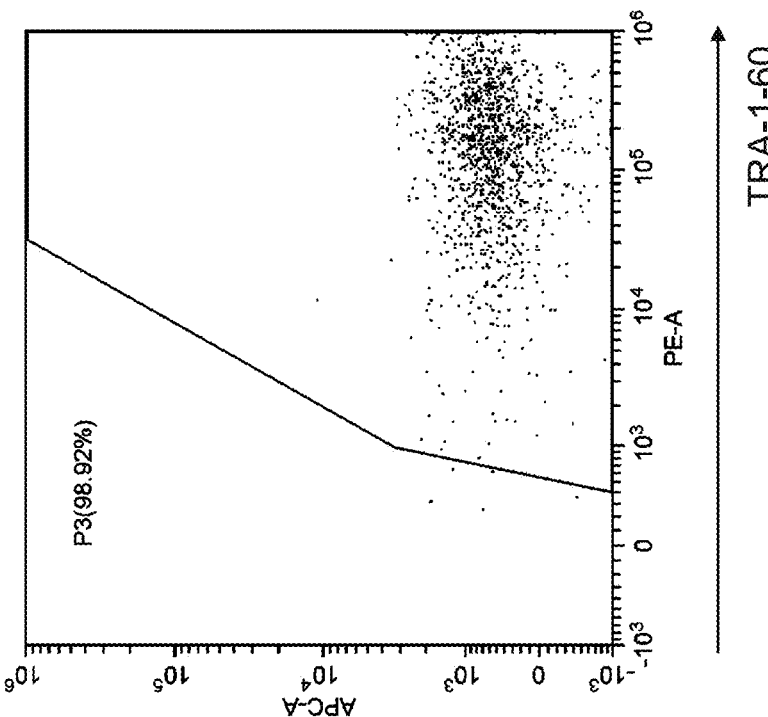
Figure 33B:
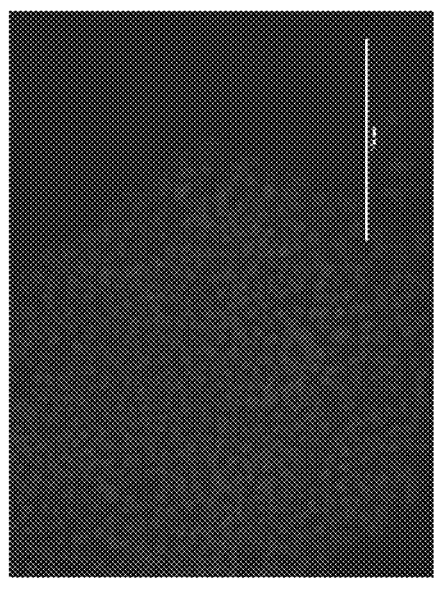
FIG. 33A to FIG. 33D show microscope images of cells according to Example 5.
Figure 33D:
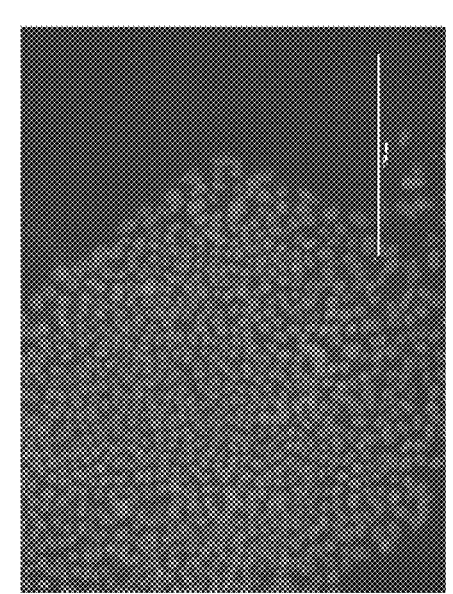
Figure 33A:
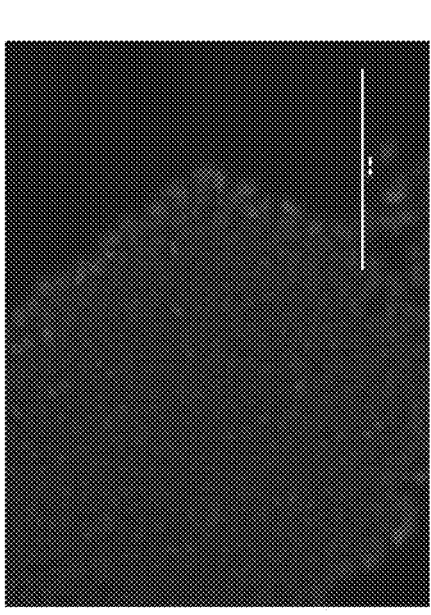
Figure 33C:
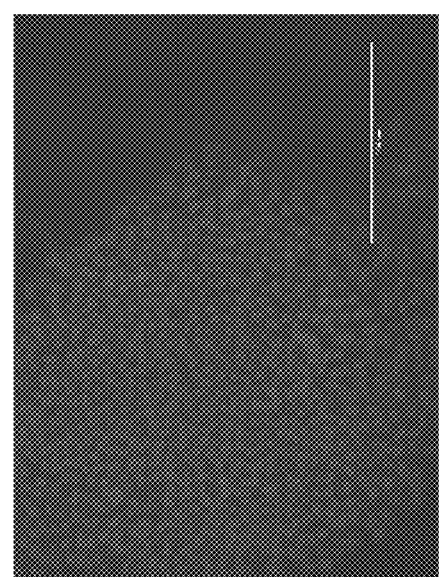

On the 13th day after the cells were seeded, in the same procedure as in Example 3, the cells were removed from the housing, some cells were collected and some cells were subcultured in the housing. During the passage, without colony picking, the removed cells were seeded in the housing without distinction. When the collected cells were analyzed with a flow cytometer, as shown in FIG. 32A, it was confirmed that the cells were TRA-1-60 positive. When the cells that have been passaged once were collected and the collected cells were analyzed with a flow cytometer, as shown in FIG. 32B, it was confirmed that the cells were TRA-1-60 positive.

In addition, when the cells that have been passaged once were collected and fixed, DNA was stained with Hoechst stain, and the cells were stained with fluorescently labeled anti-OCT3/4 antibodies and fluorescently labeled anti-NANOG antibodies, as shown in FIG. 33A to FIG. 33D, expression of OCT3/4 and NANOG, which are specific markers for pluripotent stem cells, was observed in the nuclei of the cells.

Figure 34B:
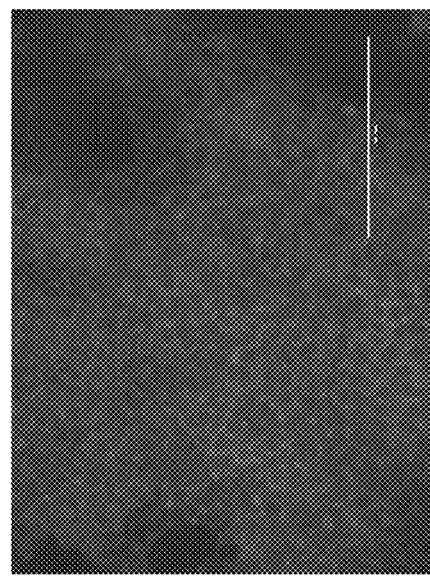
FIG. 34A to FIG. 34C show microscope images of cells according to Example 5.
Figure 34C:
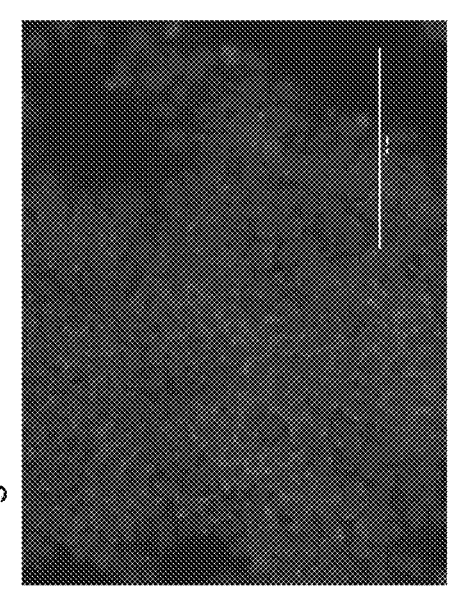
Figure 34A:
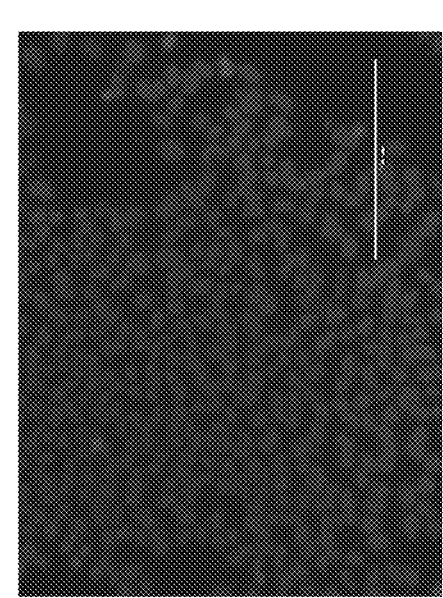

In addition, when the cells that have been passaged once were collected and fixed, DNA was stained with Hoechst stain, and the cells were stained with fluorescently labeled anti-LIN28 antibodies, as shown in FIG. 34A to FIG. 34C, expression of LIN28, which is a specific marker for pluripotent stem cells, was observed in the nuclei of the cells.

Example 6: Preparation of Induced Cells

A housing as shown in FIG. 2B was prepared, and the inside was coated with a laminin 511E8 fragment. Next, a first connection flow path of a variable volume container containing a medium in which iPS cells were suspended was sterilely bonded to a first connection flow path of the housing, and a second connection flow path of an empty variable volume container was sterilely bonded to a second connection flow path of the housing. A gas in the housing was discharged into the empty variable volume container, the medium in which the iPS cells were suspended was injected into the housing from the variable volume container containing the medium in which the iPS cells were suspended, and $1 \times 10^4$ to $1 \times 10^5$ iPS cells were seeded in the housing. Regarding the medium, a medium for stem cells was used. After the cells were seeded, each of the first connection flow path and the second connection flow path was blocked by thermocompression bonding to close the inside of the housing, the housing was placed in a thermostatic chamber at 37° C., and the cells in the housing were cultured.

The next day, a first connection flow path of a variable volume container containing a transfection medium containing a mixture of a transfection reagent and RNA encoding a drug resistance gene and a nerve cell inducing factor Ngn2 was sterilely bonded to the first connection flow path of the housing 1, and a second connection flow path of an empty variable volume container was sterilely bonded to the second connection flow path of the housing. The medium used in the housing was discharged into the empty variable volume container, and the medium for gene introduction was injected into the housing from the variable volume container containing the medium for gene introduction. Then, each of the first connection flow path and the second connection flow path was blocked by thermocompression bonding to close the inside of the housing, and the housing was placed in a thermostatic chamber at 37° C. For the next 10 days, transfection was performed once a day in the same procedure.

Figure 35:
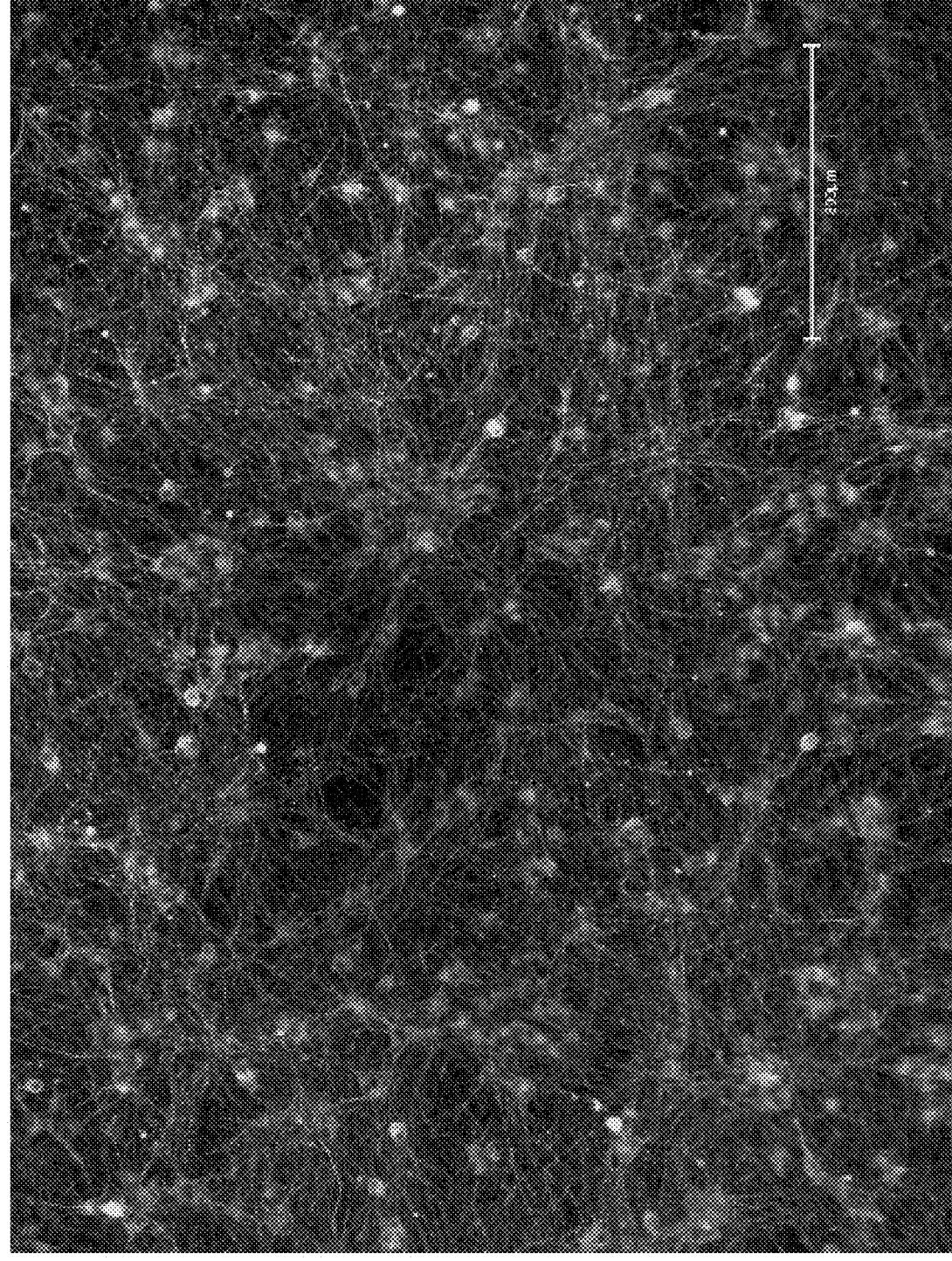
FIG. 35 is a microscope image of cells according to Example 6.

On the 2nd day after the cells were seeded, the medium in the housing was changed from the medium for stem cells to the medium for nerve cells. When the medium was replaced, a first connection flow path of a variable volume container containing a fresh medium for nerve cells was sterilely bonded to the first connection flow path of the housing, and a second connection flow path of an empty variable volume container was sterilely bonded to the second connection flow path of the housing. The medium used in the housing was discharged into the empty variable volume container, and the medium for stem cells was injected into the housing from the variable volume container 31 containing the medium for nerve cells. After the medium was replaced, each of the first connection flow path and the second connection flow path was blocked by thermocompression bonding, the inside of the housing was closed, and the housing was disposed in a thermostatic chamber at 37° C. Then, in the same procedure, the medium for nerve cells in the housing was replaced with a fresh medium for nerve cells once every 4 to 7 days. In this case, cells having drug resistance were selected. On the 21st day after the cells were seeded, as shown in FIG. 35, nerve cell-like cells in the housing were confirmed.

Example 7: Culture of Blood Cells

A housing as shown in FIG. 2B was prepared, and the inside was coated with a laminin 511E8 fragment. Next, a first connection flow path of a variable volume container containing a medium in which blood cells were suspended was sterilely bonded to the first connection flow path of the housing, and a second connection flow path of an empty variable volume container was sterilely bonded to the second connection flow path of the housing. A gas in the housing was discharged into the empty variable volume container, the medium in which the blood cells were suspended was injected into the housing from the variable volume container containing the medium in which the blood cells were suspended, and $1 \times 10^4$ to $1 \times 10^5$ blood cells were seeded in the housing. Regarding the medium, a medium for T cells or a medium for non-T cell blood cells was used. After the cells were seeded, each of the first connection flow path and the second connection flow path was blocked by thermocompression bonding to close the inside of the housing, the housing was placed in a thermostatic chamber at 37° C., and the cells in the housing were expanded and cultured.

Figures 36A, 36B:
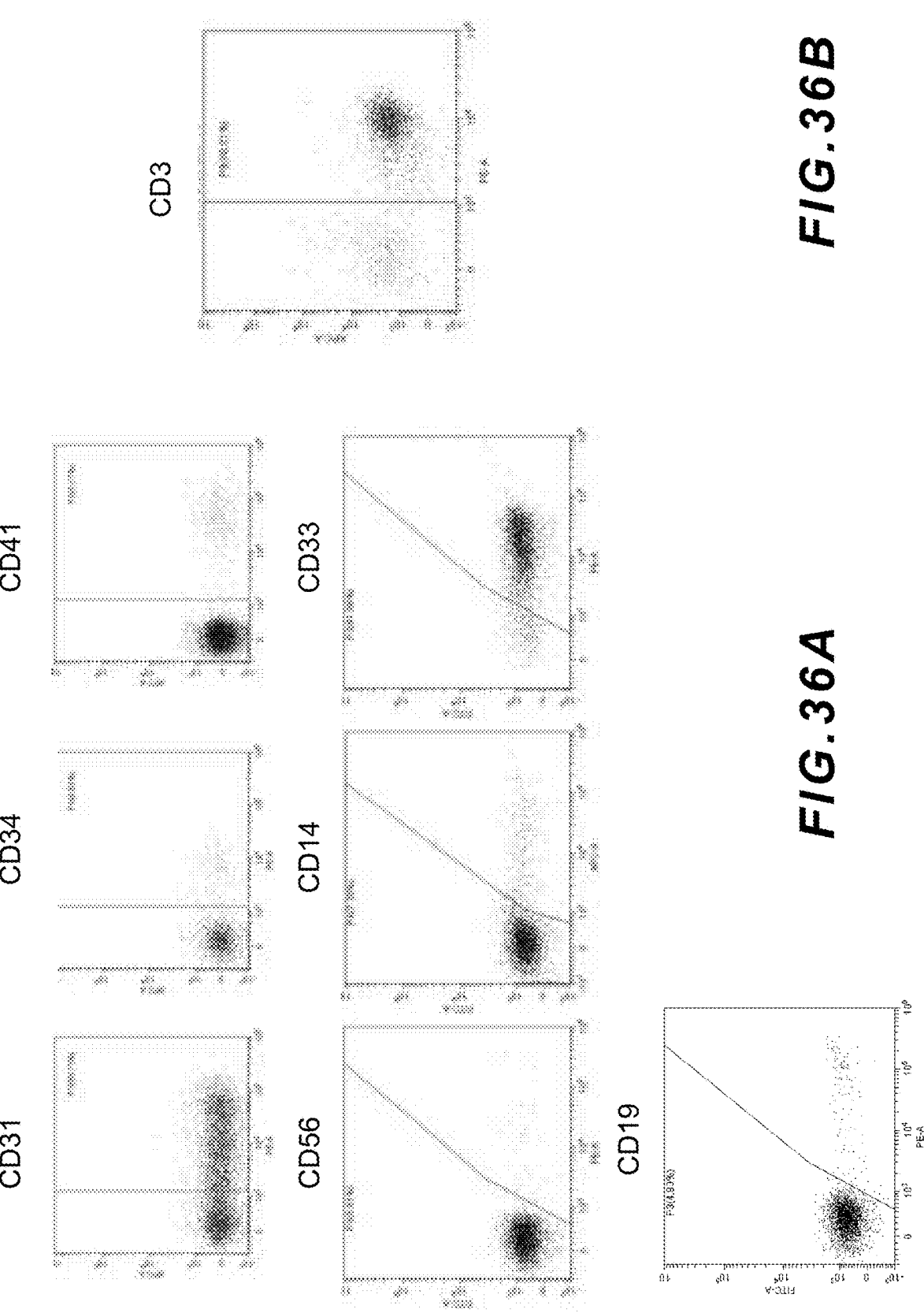
FIG. 36A and FIG. 36B show histograms showing the results of flow cytometry according to Example 7.

On the 5th day after the cells were seeded, in the same procedure as in Example 3, when the cells were removed from the housing, and the collected cells were analyzed with a flow cytometer, it was confirmed that the cells cultured in a medium for non-T cell blood cells were CD31 positive, CD34 positive, CD41 positive, CD56 positive, CD14 positive, CD33 positive, and CD19 positive as shown in FIG. 36A. It was confirmed that the cells cultured in a medium for T cells were CD3 positive as shown in FIG. 36B. Therefore, it was shown that the type of cells can be specifically selected by selecting the medium.

Example 8: Preparation of Induced Cells

A housing as shown in FIG. 2B was prepared, and the inside was coated with a laminin 511E8 fragment. Next, a first connection flow path of a variable volume container containing a medium in which iPS cells were suspended was sterilely bonded to a first connection flow path of the housing, and a second connection flow path of an empty variable volume container was sterilely bonded to a second connection flow path of the housing. A gas in the housing was discharged into the empty variable volume container, the medium in which the iPS cells were suspended was injected into the housing from the variable volume container containing the medium in which the iPS cells were suspended, and $1 \times 10^4$ iPS cells were seeded in the housing. Regarding the medium, a medium for stem cells was used. After the cells were seeded, each of the first connection flow path and the second connection flow path was blocked by thermocompression bonding to close the inside of the housing, the housing was placed in a thermostatic chamber at 37° C., and the cells in the housing were cultured.

The next day, a first connection flow path of a variable volume container containing a medium A of a cardiomyocyte induction kit (PSC Cardiomyocyte Differentiation Kit, Thermo Fisher) was sterilely bonded to the first connection flow path of the housing 1, and a second connection flow path of an empty variable volume container was sterilely bonded to the second connection flow path of the housing. The medium used in the housing was discharged into the empty variable volume container, and the medium A was injected into the housing from the variable volume container containing the medium A. Then, each of the first connection flow path and the second connection flow path was blocked by thermocompression bonding to close the inside of the housing, and the housing was placed in a thermostatic chamber at 37° C.

2 days later, a first connection flow path of a variable volume container containing a medium B of a cardiomyocyte induction kit (PSC Cardiomyocyte Differentiation Kit, Thermo Fisher) was sterilely bonded to the first connection flow path of the housing 1, and a second connection flow path of an empty variable volume container was sterilely bonded to the second connection flow path of the housing. The medium used in the housing was discharged into the empty variable volume container, and the medium. B was injected into the housing from the variable volume container containing the medium B. Then, each of the first connection flow path and the second connection flow path was blocked by thermocompression bonding to close the inside of the housing, and the housing was placed in a thermostatic chamber at 37° C.

2 days later, a first connection flow path of a variable volume container containing a cardiomyocyte maintenance medium was sterilely bonded to the first connection flow path of the housing 1, and a second connection flow path of an empty variable volume container was sterilely bonded to the second connection flow path of the housing. The medium used in the housing was discharged into the empty variable volume container, and the cardiomyocyte maintenance medium was injected into the housing from the variable volume container containing the cardiomyocyte maintenance medium. Then, each of the first connection flow path and the second connection flow path was blocked by thermocompression bonding to close the inside of the housing, and the housing was placed in a thermostatic chamber at 37° C. Then, every 1 or 2 days, the medium in the housing was replaced with a new cardiomyocyte maintenance medium.

Figure 37:
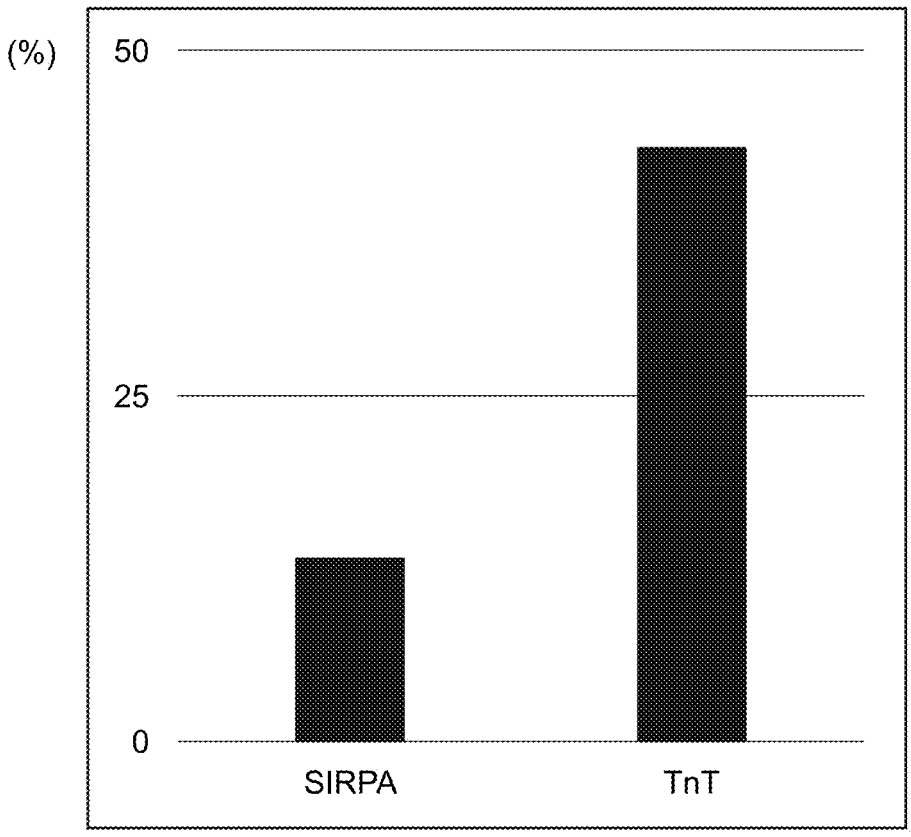
FIG. 37 is a graph showing the results of flow cytometry according to Example 8.

On the 14th day after the cells were seeded, in the same procedure as in Example 3, when the cells were removed from the housing, and the collected cells were analyzed with a flow cytometer, as shown in FIG. 37, it was confirmed that the cells were SIRPA positive and TnT positive.

Example 9: Expansion Culture of Mesenchymal Stem Cells

A housing as shown in FIG. 2B was prepared, and the inside was coated with a laminin 511E8 fragment. Next, a first connection flow path of a variable volume container containing a medium in which mesenchymal stem cells were suspended was sterilely bonded to the first connection flow path of the housing, and a second connection flow path of an empty variable volume container was sterilely bonded to the second connection flow path of the housing. A gas in the housing was discharged into the empty variable volume container, the medium in which mesenchymal stem cells were suspended was injected into the housing from the variable volume container containing the medium in which the mesenchymal stem cells were suspended, and $2 \times 10^5$ mesenchymal stem cells were seeded in the housing 1. Regarding the medium, a medium for stem cells containing a 10 µmol/L ROCK inhibitor and 10% serum was used. After the cells were seeded, each of the first connection flow path and the second connection flow path was blocked by thermocompression bonding to close the inside of the housing, the housing 1 was placed in a thermostatic chamber at 37° C., and the mesenchymal stem cells in the housing were cultured.

Figure 38:
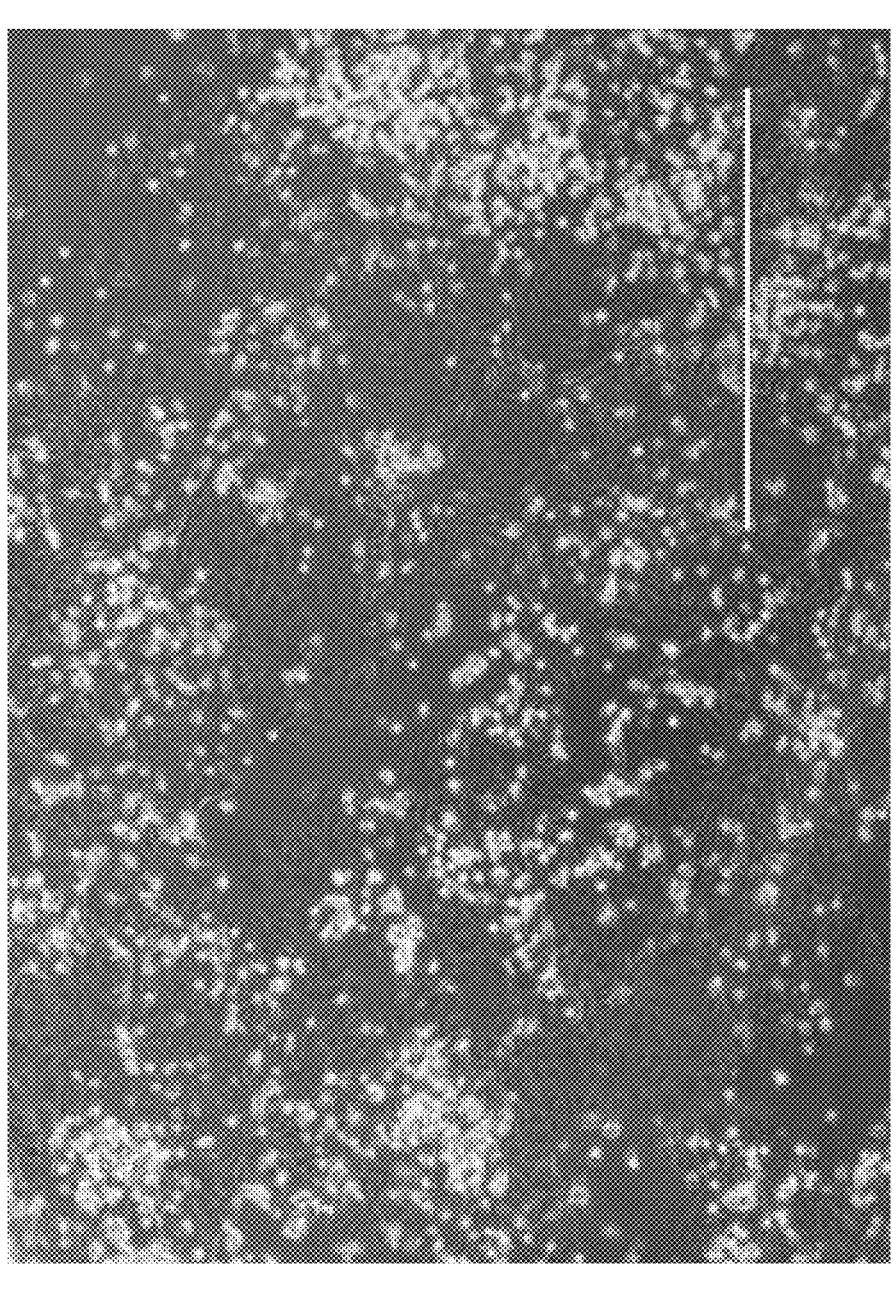
FIG. 38 is a microscope image of cells according to Example 9.

Then, the medium in the housing was replaced once every two days. When the medium was replaced, a first connection flow path of a variable volume container containing a fresh medium for stem cells was sterilely bonded to the first connection flow path of the housing, and a second connection flow path of an empty variable volume container was sterilely bonded to the second connection flow path of the housing. The medium used in the housing was discharged into the variable volume container, and the fresh medium for stem cells was injected into the housing 1 from the variable volume container 31 containing the fresh medium for stem cells. After the medium was replaced, each of the first connection flow path and the second connection flow path was blocked by thermocompression bonding, the inside of the housing was closed, and the housing was placed in a thermostatic chamber at 37° C. As a result, as shown in FIG. 38, the mesenchymal stem cells proliferated in the housing 1.

What is claimed is:

1. A method for culturing a cell, comprising:
preparing a housing in which a culture chamber is provided and a semipermeable membrane disposed in the culture chamber, the culture chamber being divided by the semipermeable membrane, wherein a first hole, a second hole, a third hole, and a fourth hole that each connect the outside of the housing and the culture chamber are provided in the housing, wherein the first hole and the second hole communicate with one side of the culture chamber divided by the semipermeable membrane, and wherein the third hole and the fourth hole communicate with the other side of the culture chamber divided by the semipermeable membrane;
contracting a first variable volume container containing a cell therein, which is connected to the first hole through a connection flow path connecting the first hole and the first variable volume container, expanding a first expandable variable volume container which is connected to the second hole through a connection flow path connecting the second hole and the first expandable variable volume container, and moving the cell into the one side of the culture chamber of the housing;
contracting a second variable volume container containing a fluid, which is connected to the third hole through a connection flow path connecting the third hole and the second variable volume container, expanding a second expandable variable volume container which is connected to the fourth hole through a connection flow path connecting the fourth hole and the second expandable variable volume container, and moving the fluid containing no cells into the other of the culture chamber of the housing;
blocking the connection flow path connecting the first hole and the first variable volume container, thereafter, removing the first variable volume container from the connection flow path;
blocking the connection flow path connecting the second hole and the first expandable variable volume container, thereafter, removing the first expandable variable volume container from the connection flow path;
blocking the connection flow path connecting the third hole and the second variable volume container, thereafter, removing the second variable volume container from the connection flow path;

blocking the connection flow path connecting the fourth hole and the second expandable variable volume container, thereafter, removing the second expandable variable volume container from the connection flow path; and placing the housing in a temperature control chamber and culturing the cell in the one side of the culture chamber of the housing.

2. A method for reprogramming a cell, comprising:

preparing a housing in which a culture chamber is provided and a semipermeable membrane disposed in the culture chamber, the culture chamber being divided by the semipermeable membrane, wherein a first hole, a second hole, a third hole and a fourth hole that each connect the outside of the housing and the culture chamber are provided in the housing, wherein the first hole and the second hole communicate with one side of the culture chamber divided by the semipermeable membrane, and wherein the third hole and the fourth hole communicate with the other side of the culture chamber divided by the semipermeable membrane;

culturing a cell in the one side of the culture chamber of the housing;

contracting a variable volume container containing a reprogramming factor therein, which is connected to the first hole through a connection flow path connecting the first hole and the variable volume container, expanding an expandable variable volume container which is connected to the second hole through a connection flow path connecting the second hole and the expandable variable volume container, and moving the reprogramming factor into the one side of the culture chamber of the housing;

blocking the connection flow path connecting the first hole and the variable volume container, thereafter, removing the variable volume container from the connection flow path;

blocking the connection flow path connecting the second hole and the expandable variable volume container, thereafter, removing the expandable variable volume container from the connection flow path; and placing the housing in a temperature control chamber and reprogramming the cell in the one side of the culture chamber of the housing.

3. A method for differentiating a cell, comprising:

preparing a housing in which a culture chamber is provided and a semipermeable membrane disposed in the culture chamber, the culture chamber being divided by the semipermeable membrane, wherein a first hole, a second hole, a third hole and a fourth hole that each connect the outside of the housing and the culture chamber are provided in the housing, wherein the first hole and the second hole communicate with one side of the culture chamber divided by the semipermeable membrane, and wherein the third hole and the fourth hole communicate with the other side of the culture chamber divided by the semipermeable membrane;

culturing a cell in the one side of the culture chamber of the housing;

contracting a variable volume container containing a differentiating factor therein, which is connected to the first hole through a connection flow path connecting the first hole and the variable volume container, expanding an expandable variable volume container which is connected to the second hole through a connection flow path connecting the second hole and the expandable variable volume, and moving the differentiating factor into the one side of the culture chamber of the housing;

blocking the connection flow path connecting the first hole and the variable volume container, thereafter, removing the variable volume container from the connection flow path;

blocking the connection flow path connecting the second hole and the expandable variable volume container, thereafter, removing the expandable variable volume container from the connection flow path; and placing the housing in a temperature control chamber and differentiating the cell in the one side of the culture chamber of the housing.

* * * * *